(12) United States Patent
Kaneko et al.

(10) Patent No.: US 6,772,003 B2
(45) Date of Patent: Aug. 3, 2004

(54) ENDOSCOPE APPARATUS

(75) Inventors: Mamoru Kaneko, Hanno (JP); Akira Hasegawa, Musashino (JP); Katsuichi Imaizumi, Hino (JP); Shunya Akimoto, Hachioji (JP); Naoki Miura, Hachioji (JP); Katsuya Ono, Hino (JP); Hideyuki Takaoka, Sapporo (JP); Kazuhiro Gono, Sagamihara (JP); Junichi Nozawa, Sagamihara (JP)

(73) Assignee: Olympus Corporation, Tokyo (JP)

( * ) Notice: Subject to any disclaimer, the term of this patent is extended or adjusted under 35 U.S.C. 154(b) by 163 days.

(21) Appl. No.: 10/207,697

(22) Filed: Jul. 29, 2002

(65) Prior Publication Data

US 2003/0040668 A1 Feb. 27, 2003

(30) Foreign Application Priority Data

Aug. 3, 2001 (JP) .................................... 2001-237075

(51) Int. Cl.$^7$ ............................................... A61B 6/00
(52) U.S. Cl. ........................................................ 600/476
(58) Field of Search ................................ 600/407–476, 600/310, 477; 356/342, 369, 367, 364; 606/7

(56) References Cited

U.S. PATENT DOCUMENTS

| 4,336,809 A | * | 6/1982 | Clark .......................... 600/478 |
| 4,515,165 A | * | 5/1985 | Carroll ........................ 600/475 |
| 4,718,417 A | * | 1/1988 | Kittrell et al. ................. 606/7 |
| 6,091,984 A |  | 7/2000 | Perelman et al. |
| 6,600,947 B2 | * | 7/2003 | Averback et al. ........... 600/476 |
| 6,697,652 B2 | * | 2/2004 | Georgakoudi et al. ...... 600/310 |

FOREIGN PATENT DOCUMENTS

WO    WO 00/42912    7/2000

OTHER PUBLICATIONS

Backman, V., et al., "Polarized Light Scattering Spectroscopy for Quantitative Measurement of Epithelial Cellular Structures In Situ", IEEE Journal of Selected Topics in Quantum Electronics, vol. 5, No. 4, pp. 1019–1026, Jul./Aug. 1999.

Gurjar, R. S., et al., "Imaging human epithelial properties with polarzied light–scattering spectroscopy", Nature Medicine, vol. 7, No. 11, pp. 1245–1248, Nov. 2001.

Harris, A.G., et al., "The study of the Microcirculation using Orthogonal Polarization Spectral Imaging", Yearbook of Intensive Care and Emergency Medicine 2000, pp. 706–714.

\* cited by examiner

*Primary Examiner*—Ali Imam
(74) *Attorney, Agent, or Firm*—Scully, Scott, Murphy & Presser

(57) ABSTRACT

A general-light observation light image can be obtained by illuminating the polarized frame sequence light or polarized white light, for example. In addition, a parallel polarized component and a vertical polarized component with respect to a polarizing direction of illuminating light, which is polarized in a specific direction are captured. Then, image data, which is a difference between both of the polarized component is calculated and is displayed in a display device. Thus, a scattered light component in a living-body tissue surface side can be extracted with good S/N, which can improve the diagnosis functionality.

30 Claims, 18 Drawing Sheets

FIG.3
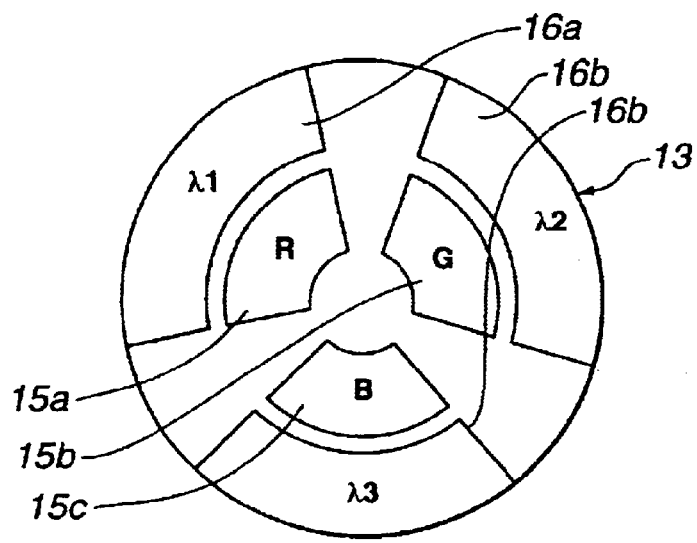
FIG.4A
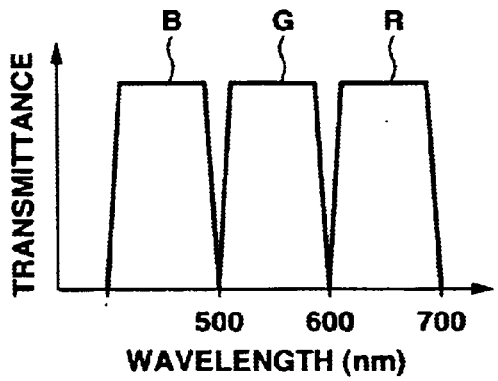
FIG.4B
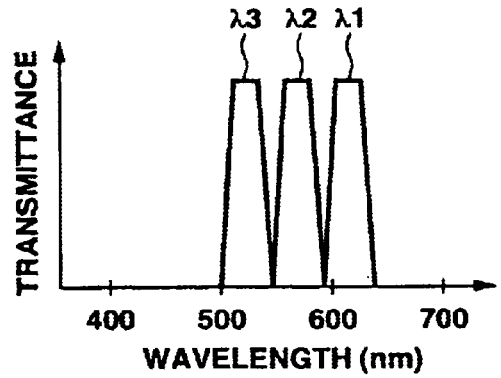
FIG.4C
WHITE LIGHT IMAGE
$W(R) = P_{//}(R) + P_{\perp}(R)$
$W(G) = P_{//}(G) + P_{\perp}(G)$
$W(B) = P_{//}(B) + P_{\perp}(B)$
SCATTERED IMAGE
$S(\lambda 1) = P_{//}(\lambda 1) - P_{\perp}(\lambda 1)$
$S(\lambda 2) = P_{//}(\lambda 2) - P_{\perp}(\lambda 2)$
$S(\lambda 3) = P_{//}(\lambda 3) - P_{\perp}(\lambda 3)$

FIG.11

| LIQUID CRYSTAL | 0° | | | 90° | | | 0° | | |
|---|---|---|---|---|---|---|---|---|---|
| ROTATING FILTER | $\lambda_1$ | $\lambda_2$ | $\lambda_3$ | $\lambda_1$ | $\lambda_2$ | $\lambda_3$ | $\lambda_1$ | $\lambda_2$ | $\lambda_3$ |
| MEMORY | FIRST FRAME MEMORY | SECOND FRAME MEMORY | THIRD FRAME MEMORY | FOURTH FRAME MEMORY | FIFTH FRAME MEMORY | SIXTH FRAME MEMORY | FIRST FRAME MEMORY | SECOND FRAME MEMORY | THIRD FRAME MEMORY |

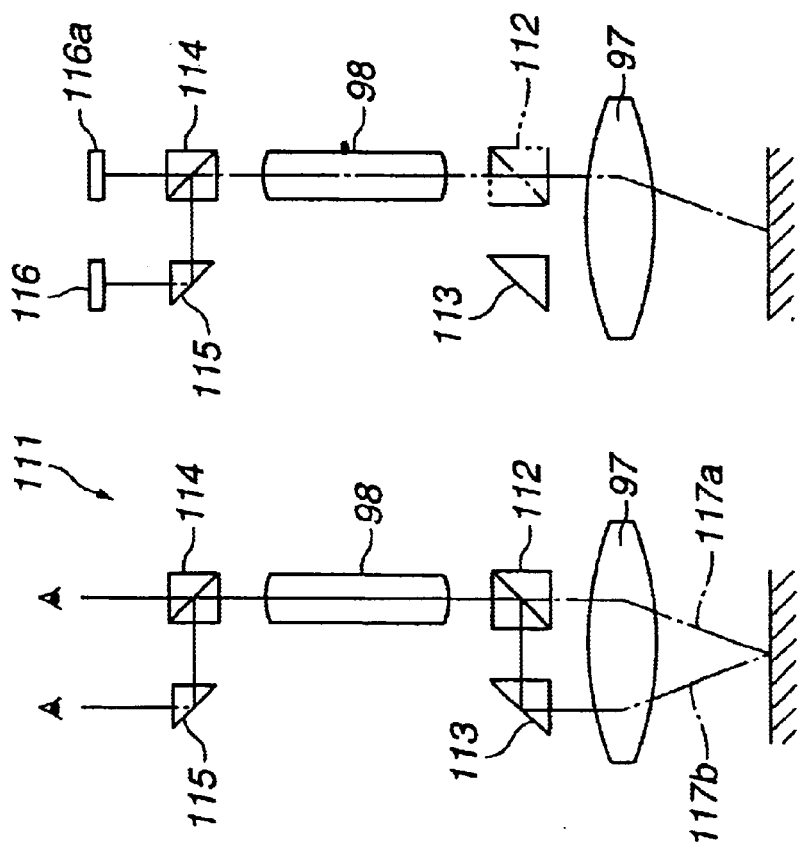
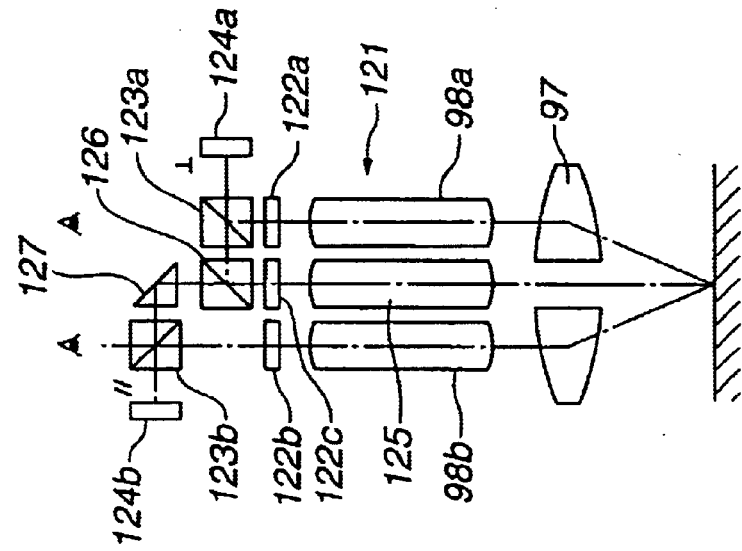

ENDOSCOPE APPARATUS

This application claims benefit of Japanese Application No. 2001-237075 filed on Aug. 3, 2001, the contents of which are incorporated by this reference.

BACKGROUND OF THE INVENTION

Field of the Invention and Description of the Related Art

The present invention relates to an endoscope device, which can obtain a general-light image and a polarized-light image using polarized light.

As a first example of the related art, there is the U.S. Pat. No. 6,091,984. The example of the related art discloses a method for determining a property of living-body tissue by irradiating light to the tissue and analyzing the spectrum of the scattered light to extract a component, which is varied depending on the size of a nucleus of a cell.

More specifically, the spectrum scattered from the living-body tissue and the spectrum scattered by the background in a model in consideration with the thickness of the tissue and blood absorption are calculated to produce the ratio. The ratio is compared with the Mie scattering theory, and the size of cell nucleus is estimated. Here, one having a larger cell nucleus is an abnormal tissue of HGD (High Grade Dysplasia), an early cancer, or the like.

In addition, as a second example of the related art, there is PCT Publication WO 00/42912.

The HGD, an early cancer or the like occurs near a surface of living-body tissue. Then, a method is disclosed for determining a property of living-body tissue wherein scattered light from the tissue surface is extracted by using polarized light, and the spectrum is analyzed. In this publication, a device shown in FIG. 1A is disclosed. Notably, FIG. 1A is cited from IEEE JOURNAL OF SELECTED TOPICS IN QUANTUM ELECTRONICS VOL. 5, NO. 4, pp. 1019–1026, by the same inventor.

In a device 130 shown in FIG. 1A, white light from a wide-band light source 131 is conducted by a fiber 132 and is converted to specific linear polarized light through a lens 133, an aperture 134 and a polarizer 135. Then, the light is entered to a beam splitter 136. The light reflected by the beam splitter 136 is irradiated to living-body tissue 137.

The light is scattered by the living-body tissue 137. The scattered light incident on the beam splitter 136, which is transparent partially, is reflected by a mirror 139 through the aperture 138 and is entered to a polarizing beam splitter 140.

A light component in a polarizing direction parallel to the direction polarized by the polarizer 135 of the light incident on the polarizing beam splitter 140 passes through the polarizing beam splitter 140 and is conducted to a multi-channel spectroscope 142 through a lens 141*a*.

A light component in a direction orthogonal to the polarizing direction by the polarizer 135 is reflected by the polarizing beam splitter 140 and is conducted to the spectroscope 142 through a lens 141*b*.

In this case, in order to prevent the reflected right from entering to the spectroscope 142 directly, the polarizing beam splitter 136 is disposed such that the illuminating light is inclined slightly with respect to the living-body tissue 137.

The parallel and vertical components are entered to spectroscope 142 by the polarizing beam splitter 140, and the difference is produced after the background correction (processing for calculating a ratio with respect to a scattering body of white light).

With this construction, light having a specific polarized component is irradiated to the living-body tissue 137. The scattered light is divided into a parallel polarized component and a vertical polarized component with respect to the polarized component of the illuminating light. Thus, the spectrum is detected. Here, the polarized component is stored in the scattered light returned from the surface of the living-body tissue 137 and becomes the polarized component parallel to the irradiated light.

Furthermore, the scattered light returned from the depths of the living-body tissue 137 is scattered strongly. Thus, the parallel component and the vertical component with respect to the irradiated light are substantially equivalent. In other words, the scattered light having parallel polarized light includes components from the surface of the living-body tissue 137 and the depths of the living-body tissue 137. The scattered light having vertical polarized light includes the component from the depths of the living-body tissue 137.

Here, by differentiating the scattered light having the parallel polarized light and the scattered light having the vertical polarized light, only scattered light on the surface of the living-body tissue 137 can be extracted. Furthermore, like the U.S. Pat. No. 6,091,984, the spectrum of the scattered light from the surface of the living-body tissue 137 is analyzed, and then the size of a cell nucleus is estimated. An advantage of this method is to allow extracting scattered light including much information relating to the size of the nucleus with good S/N by using polarized light.

FIG. 1B shows a spectrum of colon normal tissue while FIG. 1C shows a spectrum of tumor tissue. As shown in these FIGS. 1B and 1C, the strength of the scattered light increases at 600 to 650 nm once in the normal tissue. On the other hand, in the tumor tissue, the strength of the scattered light is reduced as the wavelength becomes longer. In addition, as a third example of the related art, there is A. Harris et al., "The Sturdy of the Microcirculation using Orthogonal Polarization Spectral Imaging, Yearbook of Intensive Care and Emergency Medicine 2000".

This example of the related art discloses a method for improving the contrast of a blood-vessel image by using polarized light.

More specifically, light having a specific polarized component is irradiated to tissue and the scattered light of a polarized component perpendicular to the polarized component of the illuminating light is made into an image. Here, the polarized component is stored in the scattered light returned from the tissue surface and becomes a polarized component parallel to the irradiated light. In addition, the scattered light returned from the tissue depths is strongly scattered. Thus, the parallel component and the vertical component with respected to the irradiated light are substantially equivalent.

In other words, by making into an image the light having the polarized light perpendicular to the polarizing direction of the illuminating light, the scattered light from the tissue depths can be made into an image. Thus, the scattered light from the tissue surface is reduced, as if the light were seen transparently from the depths of the tissue. As a result, the contrast of the blood vessel of the tissue surface can be improved. By using the above-described principle, a sclerotic endoscope has been developed.

In the first and the second examples of the related art, one polarized component is detected and is analyzed. Thus, image making is not described.

The third example of the related art makes into an image the light having a polarized component perpendicular to a polarizing direction of illuminating light. Thus, the light is not divided into the horizontal polarized component and the scattered light component for making an image. Furthermore, a construction for making both a general-light image and a polarized-light image is not disclosed.

OBJECTS AND SUMMARY OF THE INVENTION

It is an object of the present invention to provide an endoscope apparatus and an endoscope, which can obtain a polarized-light image by using polarized light in addition to obtain a general-light image.

It is another object of the present invention is to provide an endoscope apparatus and an endoscope, which can improve functionality of endoscope diagnoses, by including: a light source device for generating general illuminating light for obtaining a general-light image and polarized image illuminating light having a plurality of wavelength bands for obtaining a polarized-light image; an endoscope having a light conducting member for conducting the general illuminating light and the polarized image illuminating light, a polarizing member for emitting polarized illuminating light, which is polarized through the light-conducting member, to a subject side, and an image pickup device for outputting a parallel image signal and a vertical image signal captured, in the light reflected by the subject side, by using a light component in a polarizing direction parallel to a polarizing direction by the polarizing member and a light component in a polarizing direction perpendicular to the polarizing direction by the polarizing member, respectively;

an image processing device for performing image processing on at least one of the parallel image signal and the vertical image signal so that a general-light image can be displayed in a display device and for performing image processing on the parallel image signal and the vertical image signal so that a polarized-light image can be displayed in the display device, a general-light image and a polarized-light image can be obtained.

BRIEF DESCRIPTION OF THE DRAWINGS

FIGS. 2 to 4D relate to a first embodiment of the present invention; FIG. 2 is a block diagram showing an entire construction of an endoscope apparatus according to the first embodiment;

FIG. 3 is a diagram showing the construction of a rotating filter;

FIGS. 4A to 4C are diagrams showing a characteristic of a filter in the inner radius side of the rotating filter, a characteristic of a filter in the outer radius side and processing for obtaining white light and an scattered-light (polarized-light) image;

FIG. 4D is an explanatory diagram in which a part satisfying a condition for possibly affected tissue is displayed on a polarized-light image;

FIG. 6 is a block diagram showing an entire construction of an endoscope apparatus of the third embodiment;

FIG. 7 is a front view in which a distal-end cap is viewed from the endoscope side;

FIG. 8 is a diagram showing a construction of a rotating filter;

FIGS. 10 to 12B relate to a fifth embodiment of the present invention; FIG. 10 is a block diagram showing an entire construction of an endoscope apparatus according to the fifth embodiment;

FIG. 11 is an explanatory diagram of an operation in a polarized light observation mode according to the embodiment;

FIG. 12B is a view of FIG. 12A viewing from the above;

FIG. 13 is a diagram showing a construction of an endoscope distal end side according to the sixth embodiment;

FIG. 14 is an explanatory diagram of an operation in a polarized light observation mode;

FIGS. 16A to 17 relate to an eighth embodiment of the present invention; FIG. 16A is a diagram showing a construction of an endoscope distal end side according to the eighth embodiment;

FIG. 17 is a diagram showing a construction of an illuminating optical system in an endoscope distal end side in a variation example;

FIG. 19 is a block diagram showing an entire construction of an endoscope apparatus according to the tenth embodiment;

FIG. 20 is an explanatory diagram of an operation;

FIGS. 21 to 26 relate to an eleventh embodiment of the present invention; FIG. 21 is a diagram of a construction of a compound-eye stereoscopic endoscope according to the eleventh embodiment;

FIG. 22 is a diagram showing a construction of a compound-eye stereoscopic endoscope of a first variation example;

FIG. 23 is a diagram showing a construction of a compound-eye stereoscopic endoscope of a second variation example;

FIG. 24 is a diagram showing a part for rotating a polarizer;

FIG. 25A is a diagram showing a case where a polarizing beam splitter is installed in a construction of a compound-eye stereoscopic endoscope of a third variation example;

FIG. 25B is a diagram showing a case where a polarizing beam splitter is installed in a construction of a compound-eye stereoscopic endo scope of a third variation example; and FIG. 26 is a diagram showing a construction of a compound-eye stereoscopic endoscope of a fourth variation example.

DETAILED DESCRIPTION OF THE PREFERRED EMBODIMENTS

Embodiments of the present invention will be described below with reference to drawings.

(First Embodiment)

A first embodiment of the present invention will be described with reference to FIGS. 2 to 4D. It is an object of this embodiment to provide an endoscope apparatus, which can pick up both polarized-light image and general-light image.

Figure 2:
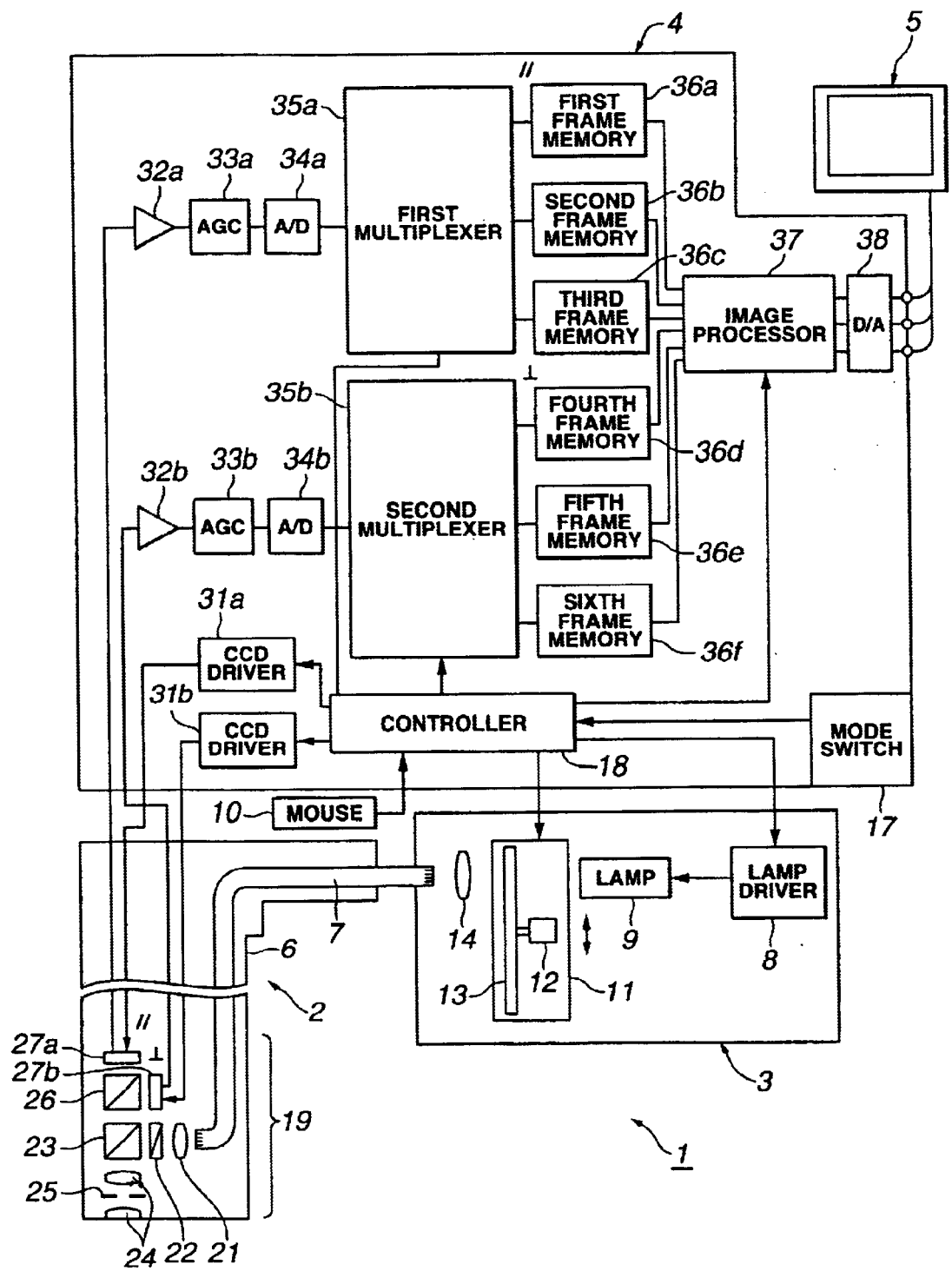

An endoscope apparatus 1 for polarized-light observation according to the first embodiment of the present invention shown in FIG. 2 is inserted to a body cavity and includes an endoscope 2 for picking up a general-light image and a polarized-image, a light source device 3 for supplying illuminating light to the endoscope 2, a processor 4 for performing signal processing on an image pickup element, which is built in the endoscope 2, and a monitor 5 for displaying video signals output from the processor 4.

The endoscope 2 is provided with a long and narrow inserting portion 6, which can be inserted into a body cavity, for example. A light guide 7 as a transmitting member (conducting member) for transmitting (conducting) illuminating light is inserted through the inserting portion 6. An end portion in the proximal end side of the light guide 7 can be connected to the light source device 3 removably.

A lamp 9, such as xenon lamp, for emitting light in response to a lamp drive signal from a lamp drive circuit 8 is disposed within the light source device 3. White light emitted by the lamp 9 passes through a rotating filter 13, which is mounted on a movable stage 11 and is rotationally driven by a motor 12, and is collected by a focusing lens 14. Then, the light is entered to an end portion in the proximal end side of the light guide 7.

As shown in FIG. 3, the rotating filter 13 is provided with a filter for general-light observation and a filter for polarized-light observation in the inner radius side and in the outer radius side respectively.

In other words, R, G, and B filters 15a, 15b and 15c for passing through light in wavelength bands of red (R), green (G) and blue (B), respectively, are disposed in the inner radius side so as to divide into three in circumferential direction. Wavelength transmittance characteristics of the R, G and B filters 15a, 15b and 15c are shown in FIG. 4A. Here, they are indicated by R, G and B (rather than 15a, 15b and 15c).

More specifically, the R filter 15a passes through red light in 600 to 700 nm of wavelength band. The G filter 15b passes through green light in 500 to 600 nm of wavelength band. The B filter 15c passes through blue light in 400 to 500 nm of wavelength band.

Furthermore, as shown in FIG. 3, filters 16a, 16b and 16c for passing through light in three wavelength bands (indicated by $\lambda 1$, $\lambda 2$ and $\lambda 3$), respectively, as shown in FIG. 4B are disposed in the outer radius side so as to divide into three in circumferential direction. Respective transmitting bands are set for the filters 16a, 16b and 16c from the band 450 nm to 650 nm. Notably, they are remarked by $\lambda 1$, $\lambda 2$ and $\lambda 3$ in FIG. 4B.

More specifically, the filter 16a passes through light in 600 to 650 nm of wavelength band. The filter 16b passes through light in 550 to 600 nm of wavelength band. The filter 16c passes through light in 500 to 550 nm of wavelength band.

Figure 1A:
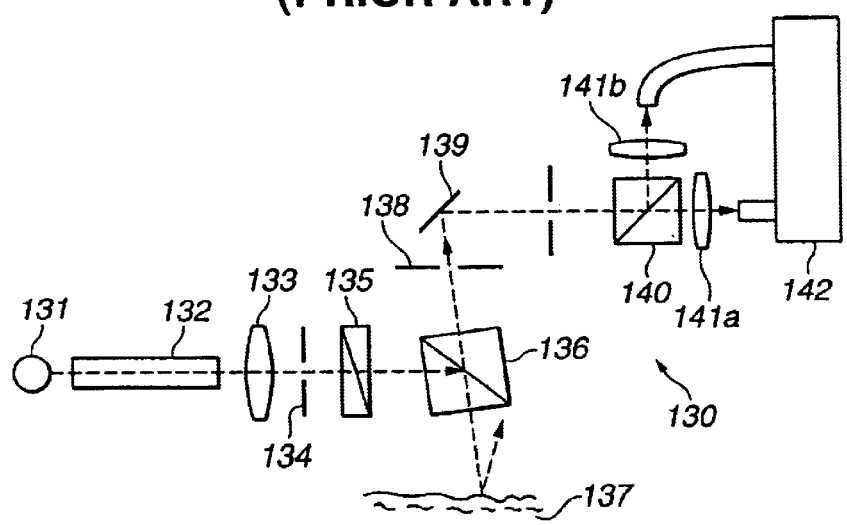
FIGS. 1A to 1C are diagrams showing an apparatus using polarized light according to an example of the related art and properties of spectrum strength in cases of normal tissue and tumor tissue, respectively.
Figure 1B:
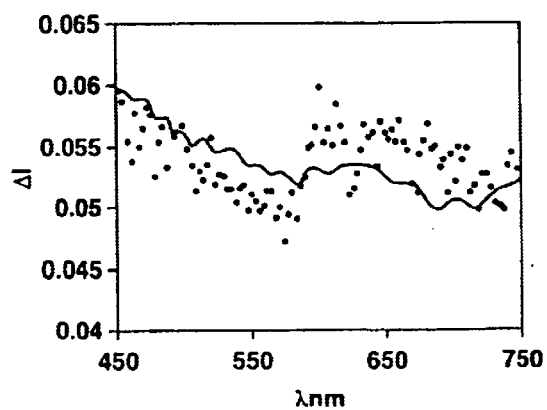
Figure 1C:
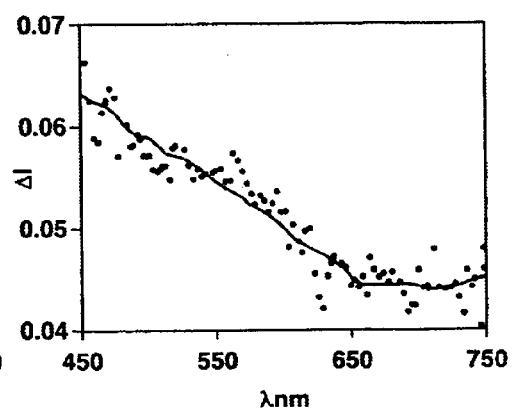

The transmitting wavelength bands of these filters 16a, 16b and 16c are set in accordance with the characteristics in FIGS. 1B and 1C.

Figure 5:
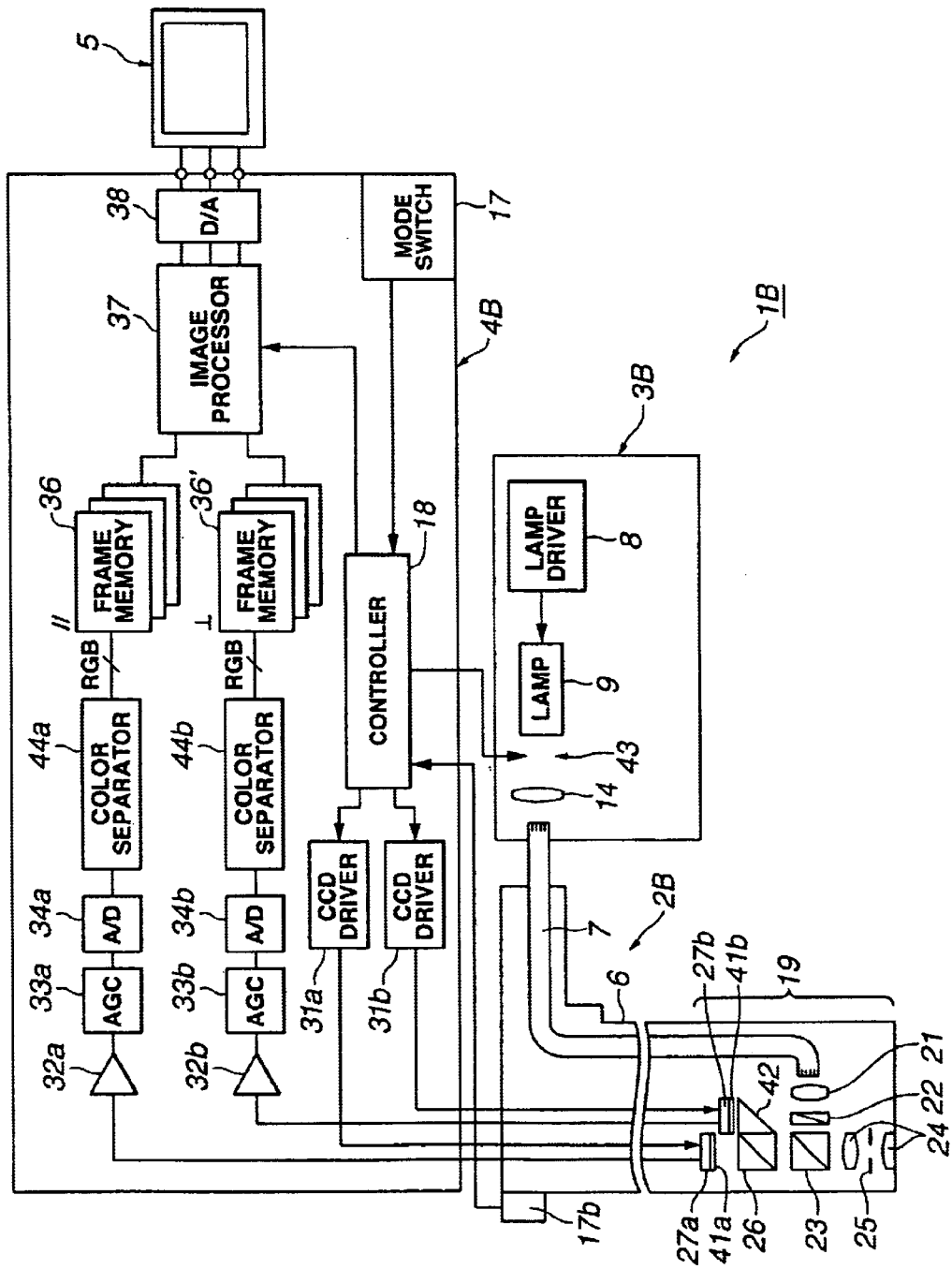
FIG. 5 is a block diagram showing an entire construction of an endoscope apparatus according to a second embodiment of the present invention.

In an initial state, the filter in the inner radius side of the rotating filter 13 is set so as to dispose on an illuminating light path. When a mode for performing polarized-light observation is selected by using a mode switch 17 provided in the video processor 4, for example, the movable stage 11 is moved to the bottom side through a control circuit 18 within the video processor 4. Thus, the filter in the outer radius side of the rotating filter 13 is disposed on the illuminating light path. As shown in FIG. 5 (a second embodiment), which will be described later, the mode switch 17 may be provided in the endoscope side.

Furthermore, when the general-light observation is desired again after setting to the mode for performing polarized-light observation, and when the mode for performing general-light observation is selected by using the mode switch 17, the movable stage 11 is moved to the upper side through the control circuit 18 within the video processor 4. Thus, the filter in the inner radius side of the rotating filter 13 is disposed on the illuminating light path.

Light incident on the light guide 7 is emitted from a distal-end surface, which is filed to a distal end portion 19 of the inserting portion 6. The light is polarized in a predetermined direction from the distal end surface, which is bent in this embodiment, through a lens 21 and a polarizer 22, which is a polarizing member for producing polarized light. Then, the light is reflected partially by a beam splitter (abbreviated as BS hereinafter) 23 and is irradiated to the subject side, such as living-body tissue, through an objective lens system 24, which is also used for illumination. Notably, an aperture 25 is provided in the objective lens system 24.

As described above, in the general-light observation mode, the subject side is sequentially illuminated by R, G and B illuminating light. On the other hand, in the polarized-light observation mode, the subject side is sequentially illuminated by $\lambda 1$, $\lambda 2$ and $\lambda 3$ illuminating light.

The light, which is reflected by the illuminated subject side and then enters to the objective lens system 24, passes through the BS 23 partially and is separated into a polarized light component (which is remarked by // in FIG. 2 and so on for easy understanding) parallel to a direction polarized by the polarizer 22 and a polarized light component (which is remarked by ⊥ in FIG. 2 and so on for easy understanding) orthogonal to the direction by using a polarizing beam splitter (abbreviated as PBS hereinafter) 26, which is a light-detecting member.

In other words, the light of the parallel polarized component passes through the PBS 26 and the image is formed in a first CCD 27a, which is disposed at an image-forming position of the objective lens system 24. The light of the orthogonal polarized component passes through the PBS 26 and the image is formed in a second CCD 27b, which is disposed at an image-forming position of the objective lens system 24. Each of them is photoelectrically converted.

The photoelectrically converted signal charges are read out by applying CCD drive signals from CCD drive circuits 31a and 31b within the video processor 4 to the CCD's 27a and 27b. After the read signal charges are amplified in preamplifiers 32a and 32b, respectively, they are further amplified in AGC circuits 33a and 33b to a predetermined level. Then, they are input to A/D converting circuits 34a and 34b and are converted to digital signals (image data).

The digital image data, which is converted by the A/D converting circuits 34a and 34b, is sequentially written in first through third frame memories 36a to 36c and in fourth through sixth frame memories 36d to 36f through first and second multiplexer 35a and 35b, respectively.

Notably, in order to write in the first through third frame memories 36a to 36c and in the fourth through sixth frame memories 36d to 36f, switching the first and the second multiplexers 35a and 35b are controlled by the control circuit 18.

The image data written in these first through sixth frame memories 36a to 36f are read out simultaneously and are input to an image processing circuit 37. The image processing circuit 37 is controlled by the control circuit 18 and performs image processing in accordance with a mode set by the mode switch 17. The image processing circuit 37 outputs image-processed image data to the D/A converting circuit 38. Then, analog vide signals converted by the D/A converting circuit 38 are output to a monitor 5.

For example, in the general-light observation mode, image components captured in the same wavelength are added and output. In the polarized-light observation mode, a difference between image components picked up in the same wavelength is produced, and the differential component is output.

Notably, in the polarized-light observation mode, for example, the control circuit 18 controls the lamp drive circuit 8 to increase an amount of light emitted by the lamp 9. Notably, a keyboard or mouse 10 is connected to the control circuit 18 such that data input, instruction input and/or area specification can be performed.

In this way, this embodiment is characterized in that a general-light image and a polarized-light image, which is suitable for determining a property near a surface of living-body tissue, as described later, by using polarized-light illuminating light, can be obtained.

An operation of this embodiment will be described next. As shown in FIG. 2, the endoscope 2, the light source device 3, the video processor 4 and the monitor 5 are connected and are powered on. In the initial state, the movable stage 11 of the light source device 3 is set in the upper side. The filter for general-light observation of the rotating filter 13 is set on the illuminating light path.

Then, the rotating filter 13 is rotated by the motor 12. The R, G and B illuminating light beams from the light source device 3 are sequentially supplied to the light guide 7 and are transmitted by the light guide 7. Then, these lights are irradiated to a subject side by being polarized from the distal end surface through the polarizer 22.

A part of reflected light, which is reflected by the subject side, enters to the objective lens system 24. The parallel component light passes through the PBS 26 and the image is formed in the CCD 27a. The orthogonal component light is reflected by the PBS 26 and the image is formed in the CCD 27b.

The signals photoelectrically converted by the CCD 27a and 27b, respectively, are read out by applying CCD drive signals from CCD drive circuits 31a and 31b. After the read signals are amplified in the preamplifiers 32a and 32b, respectively, they are converted to digital signals in the A/D converting circuits 34a and 34b. Then, the digital signals are sequentially written in first through third frame memories 36a to 36c and in the fourth through sixth frame memories 36d to 36f through the first and second multiplexers 35a and 35b, respectively, which are switched by the control circuit 18.

More specifically, output signals of the CCD's 27a and 27b are stored in the first frame memory 36a and the fourth frame memory 36d under a state where the R light is illuminated thereto. Output signals of the CCD's 27a and 27b are stored in the second frame memory 36b and the fifth frame memory 36e under a state where the G light is illuminated thereto. Output signals of the CCD's 27a and 27b are stored in the third frame memory 36c and the sixth frame memory 36f under a state where the B light is illuminated thereto.

Image data written in these first through sixth frame memories 36a to 36f is read out simultaneously and is input to the image processing circuit 37. Output signals from the first frame memory 36a and from the fourth frame memory 36d are added in the image processing circuit 37, which is output as an R color signal. Output signals from the second frame memory 36b and from the fifth frame memory 36e are added therein, which is output as a G color signal. Output signals from the third frame memory 36c and from the sixth frame memory 36f are added therein, which is output as a B color signal.

In other words, in order to create a general-light observation image (white light image) in the general-light observation mode, the general observation image is obtained through addition processing in the image processing circuit 37 as shown in the left-hand side of FIG. 4C, where the R, G and B image components are indicated by W(R), W(G) and W (B), image components output from the first through third frame memories 36a to 36c are indicated by P//(R), P//(G) and P//(B), and image components output from the fourth through sixth frame memories 36d to 36f are indicated by P⊥(R), P⊥(G) and P⊥(B).

In the general-light observation mode, by adding two polarized image components, an image with good S/N can be obtained, which is brighter than that formed by one polarized-light image component only. When an amount of illuminating light is enough, only one polarized-light image component may be used for the image display.

For example, only the (parallel) polarized-light image components P//(R), P//(G) and P//(B) output from the first through third frame memories 36a to 36c or the (vertical) polarized-light image components P⊥(R), P⊥(G) and P⊥(B) output from the fourth through sixth frame memories 36d to 36f may be used for the image display.

For example, affected tissue within a body cavity can be observed in the general-light observation mode and can be diagnosed by using a general endoscope image. When there is a need to determine a more detail property of the part, the polarized-light observation mode may be adopted. The polarized-light observation mode is set by using the mode switch 17.

When an instruction input for the polarized-light observation mode is performed by using the mode switch 17, the control circuit 18 moves the movable stage 11 of the light source device 3 to the bottom such that the filter for the polarized-light observation can be disposed on the optical path. In addition, a control signal for switching to processing for the polarized-light observation is sent to the image processing circuit 37.

In this case, the light passing through the rotating filter 13 becomes λ1, λ2 and λ3 light beams instead of R, G and B light beams, as described above. Then, these light beams are polarized by the polarizer 22 and are irradiated to the affected tissue.

In this case, most reflected light near the surface of the affected tissue, which stores illuminating light in the polarizing direction, becomes substantially dominant. On the other hand, the reflected light from a more inner part than the part near the surface has the parallel component and the vertical component with respect to the polarizing direction of the illuminating light, of which proportions are substantially the same.

These kinds of reflected light form images, respectively, in accordance with the polarizing direction. That is, the light parallel to the polarizing direction of the irradiated light forms an image in the CCD 27a while the light perpendicular to the polarizing direction of the irradiated light forms an image in the CCD 27b. Like the one described in the general-light observation mode, the signals photoelectrically converted in the CCD's 27a and 27b are written in the first through third frame memories 36a to 36c and the fourth through sixth frame memories 36d to 36f, respectively.

More specifically, output signals of the CCD's 27a and 27b are stored in the first frame memory 36a and the fourth frame memory 36d under a state where λ1 light is illuminated. Output signals of the CCD's 27a and 27b are stored in the second frame memory 36b and the fifth frame memory 36e under a state where λ2 light is illuminated. Output signals of the CCD's 27a and 27b are stored in the third frame memory 36c and the sixth frame memory 36f under a state where λ3 light is illuminated.

These image data written in the first through sixth frame memories 36a to 36f are read out simultaneously and are input to the image processing circuit 37. In this mode, a difference of output signals from the first frame memory 36a and the fourth frame memory 36d is calculated and is output as an R color signal, for example. A difference of output signals from the second frame memory 36b and the fifth frame memory 36e is calculated and is output as a G color signal, for example. A difference of output signals from the third frame memory 36c and the sixth frame memory 36f is calculated and is output as a B color signal, for example.

In other words, in order to create a polarized-light observation image (scattered image in the polarized-light observation mode, a polarized-light observation image (scattered image) is obtained as shown in the right-hand side of FIG. 4C where three image components λ1, λ2 and λ3 are $S(\lambda 1)$, $S(\lambda 2)$ and $S(\lambda 3)$, image components output from the first through third frame memories 36a to 36c are $P//(\lambda 1)$, $P//(\lambda 2)$ and $P//(\lambda 3)$, and image components output from the fourth through sixth frame memories 36d to 36f are $P\perp(\lambda 1)$, $P\perp(\lambda 2)$ and $P\perp(\lambda 3)$.

In this case, an image component in the side near the surface of the affected tissue can be obtained as the polarized-light observation image by suppressing a scattering effect from the inside.

Also, it is easy to determine properties of normal tissue and affected tissue from the characteristic of the strength with respect to the wavelength in this case. More specifically, as seen from the characteristics in FIGS. 1B and 1C, a large change cannot be found in strength with respect to the wavelength for the normal tissue. However, for the affected tissue, the wavelength dependency is shown that the strength tends to be decreased as the length of the band of the wavelength is increased.

Therefore, also in this embodiment, by examining the tendency of the strength in three wavelength bands from the shorter wavelength to the longer wavelength, it is easy to diagnose whether it is normal tissue or affected tissue.

More specifically, by comparing the strength between $S(\lambda 1)$ and $S(\lambda 2)$ or $S(\lambda 1)$ and $S(\lambda 3)$, for example, it is easy to determine whether or not it is changed. Thus, by displaying images (where they are $T(\lambda 1-\lambda 2)$ and $T(\lambda 1-\lambda 3)$, for example), which are produced from the differences between $S(\lambda 1)$ and $S(\lambda 2)$, $S(\lambda 1)$ and $S(\lambda 3)$, respectively, and by mainly diagnosing a part exposing a wavelength dependency that $T(\lambda 1-\lambda 3)$ is larger than $T(\lambda 1-\lambda 2)$, for example, it is possible to find the affected tissue efficiently.

Figure 4D:
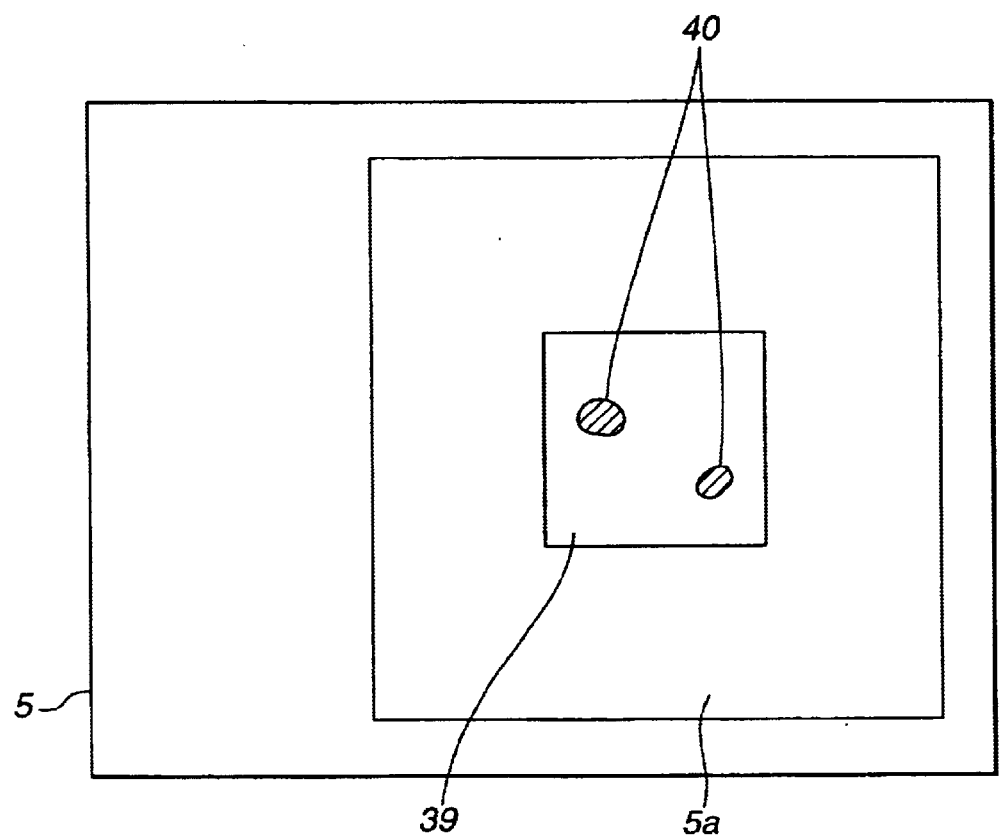

FIG. 4D shows a state where a polarized-light observation image is displayed in a polarized-light observation image display area 5a of the monitor 5. A user specifies an interested area 39 by using, for example, the mouse 10 as a pointing device on this screen. In response to this, the control circuit 18 instructs the image processing circuit 37 to calculate $T(\lambda 1-\lambda 2)$ and $T(\lambda 1-\lambda 3)$ with respect to the image part within the interested area 39. The image processing circuit 37 performs the instructed calculation and outputs a part 40 corresponding to the condition, $T\lambda 1-\lambda 3)>T(\lambda 1-\lambda 2)$ by using a specific color signal such that the part 40 can be displayed in conspicuous color, for example, on the monitor 5.

The user can diagnose the part 40 very carefully when the part 40 satisfying the condition indicating possible affected tissue is displayed.

While the interested area 39 is specified in the center part, for example, in FIG. 4D, the same processing and display may be performed on the display area 5a entirely.

In this way, according to this embodiment, a general endoscope image can be obtained. In addition, a polarized-light image can be obtained, from which the property indicating the presence of a change can be diagnosed easily by using polarized light.

Therefore, in addition to the diagnose function by using a general endoscope image, the determination of the property indicating the presence of a change can be performed by using a polarized-light image. Thus, the function by an endoscope examination can be improved more.

(Second Embodiment)

Next, a second embodiment of the present invention will be described with reference to FIG. 5. FIG. 5 shows an endoscope apparatus 1B according to the second embodiment. The endoscope apparatus 1B includes an endoscope 2B for performing full-color image capturing under white light, a light source device 3B for generating white light, a vide processor 4B for performing signal processing on an image pickup element of the endoscope 2B, and a monitor 5.

The endoscope 2B forms a CCD for full-color image capturing having color separating filters 41a and 41b on image capturing surfaces of the CCD's 27a and 27b, respectively, of the endoscope 2 in FIG. 2.

Also, in the endoscope 2B, light reflected by the PBS 26 is reflected by a triangular prism 42. Then, image capturing is achieved by the CCD 27b disposed in parallel with the CCD 27a. Furthermore, a mode switch 17b is provided in the endoscope 2B. A signal generated when it is manipulated is input to the control circuit 18 in the same manner as the case where the mode switch 17 is manipulated.

The light source device 3B supplies, in the light source device 3 of FIG. 2, the light guide 7 with white light of the lamp 9 passing through the light amount aperture 43 and the focusing lens 14.

Notably, the control circuit 18 controls to increase a light amount of the light amount aperture 43 for the case of the polarized-light observation mode in comparison with the case of the general-light observation mode.

The video processor 4B includes color separating circuits 44a and 44b for performing color separation on output signals from the A/D converting circuits 34a and 34b in the vide processor 4 in FIG. 2. Thus, the output signals are stored in frame memories 36 and 36'.

The color separating circuits 44a and 44b perform color separation to create R, G and B signals, for example, and store them in the frame memories 36 and 36' having three plane memories, respectively. Color component signals read out from the frame memories 36 and 36' are input to the image processing circuit 37. After substantially the same image processing as that of the first embodiment is performed thereon, the signals are output to the monitor 5 through the D/A converting circuit 38.

This embodiment performs full-color image capturing and the signal processing(image processing), and polarized-light image capturing and the signal processing (image processing) under the white light.

Thus, in the general-light observation mode, substantially the same operation is performed except that frame sequence type illumination and the frame sequence type image capturing under the state according to the first embodiment are replaced by the simultaneous illumination and image capturing.

Also in the polarized-light observation mode, the frame sequence type illumination and the frame sequence type image capturing under the state according to the first embodiment are replaced by the simultaneous illumination and image capturing. The wavelength bands in that case are changed from $\lambda 1$, $\lambda 2$ and $\lambda 3$ to B, G and R.

This embodiment has substantially the same effect as that of the first embodiment.

(Third Embodiment)

A third embodiment of the present invention will be described next with reference to FIGS. 6 to 8. It is an object of this embodiment to provide an endoscope apparatus, which can obtain a polarized-light image and a general-light image by using an existing endoscope.

Figure 6:
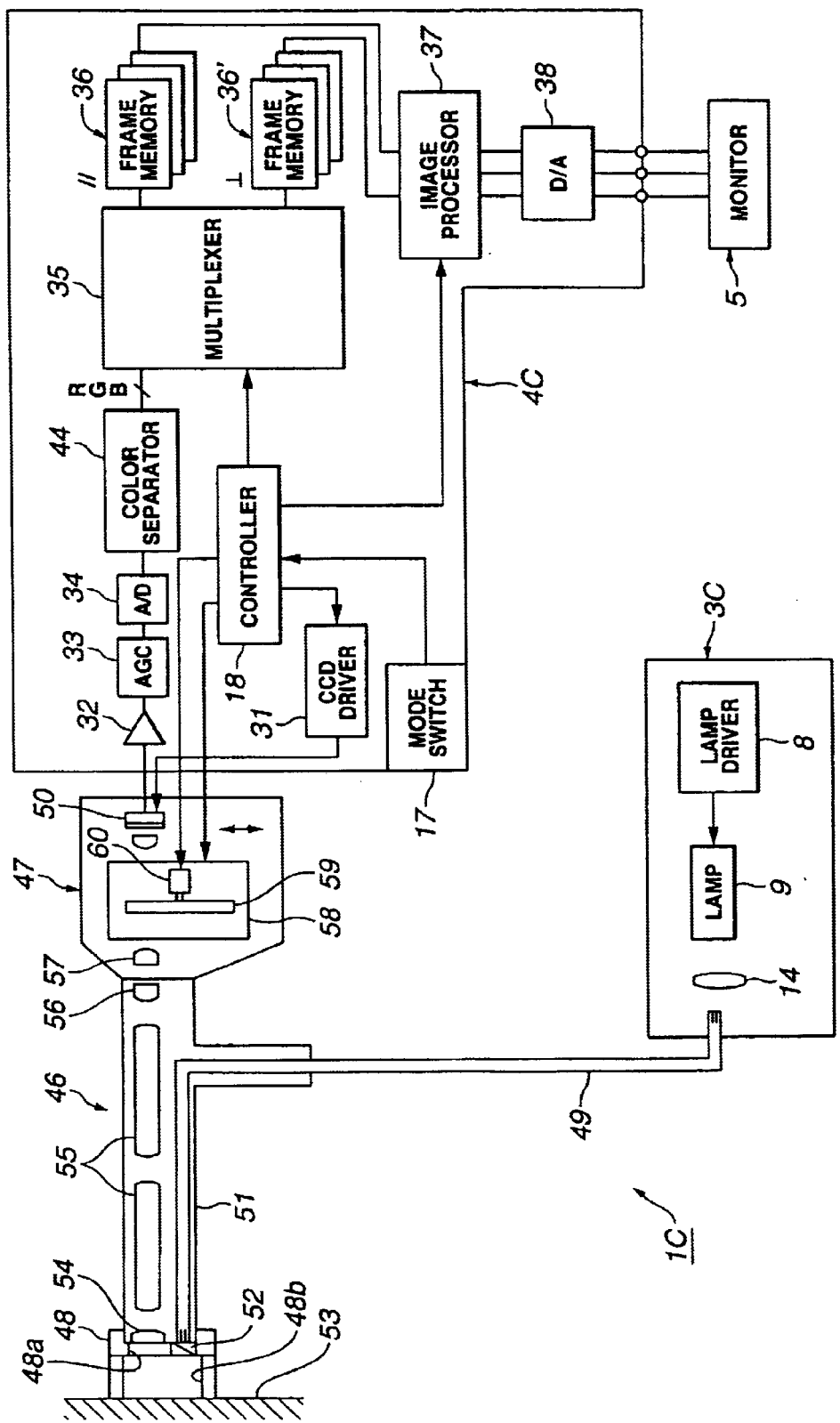
FIGS. 6 to 8 relate to a third embodiment of the present invention.

FIG. 6 shows an endoscope apparatus 1C according to the third embodiment. The endoscope apparatus 1C includes an optical endoscope 46, an external camera 47, which is mounted at the back end of the optical endoscope 46, a distal-end cap 48, which is mounted at the distal end of the optical endoscope 46, a light source device 3C for supplying illuminating light to a light guide 49 of the optical endoscope 46, a processor 4C for performing signal processing on a full-color CCD 50 of the external camera 47 and the monitor 5.

The optical endoscope 46 transmits white light supplied from the light source device 3C by using the light guide 49, which is inserted through an inserting portion 51, for example. Then, the light is irradiated from the distal end surface fixed in an illuminating window to a subject 53 side of affected tissue through a polarizer 52, which is provided in the distal-end cap 48.

Figure 7:
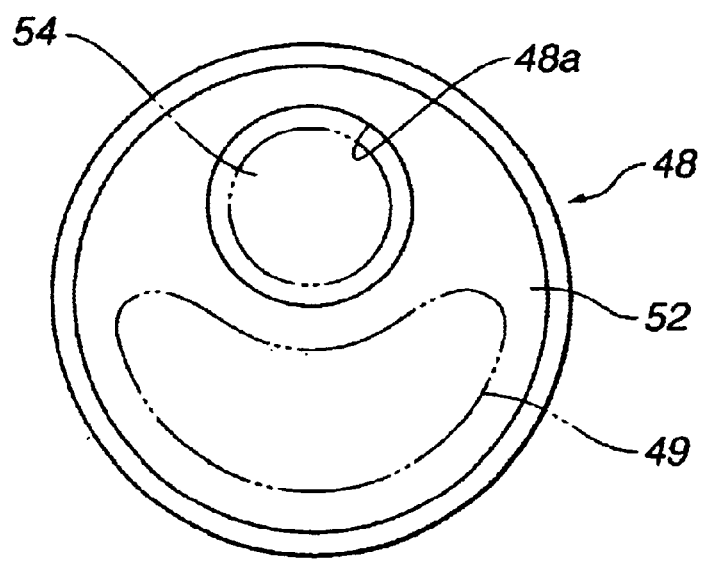

The polarizer 52 is pasted in a side of the distal end cap 48 facing with the distal end surface of the light guide 49, as shown in FIG. 7, for example. Then, illuminating light from the distal end surface of the light guide 49 is polarized. In addition, an aperture 48a is provided in a part facing with an objective lens 54 mounted in an observation window adjacent to the illuminating window. Thus, light from the subject 53 side is conducted to the objective lens 54.

A water-accommodating portion 48b is provided in the distal end cap 48. Thus, an endoscope examination can be performed by abutting the distal end surface with the surface of the subject 53 under a condition where water is accommodated. As a result:

An image through the objective lens 54 is transmitted to the backward ocular portion side through a relay lens 55. Then, the image is formed in the full-color CCD 50 after being passed through an image-forming lens 57, which is provided in the external camera 47 by facing with the ocular lens 56, and a rotating filter 59 in a movable stage 58, and then is photoelectrically converted in the full-color CCD 50.

A motor 60 for rotationally driving the rotating filter 59 and the movable stage 58 are controlled by a control circuit 18 of the processor 4C.

Figure 8:
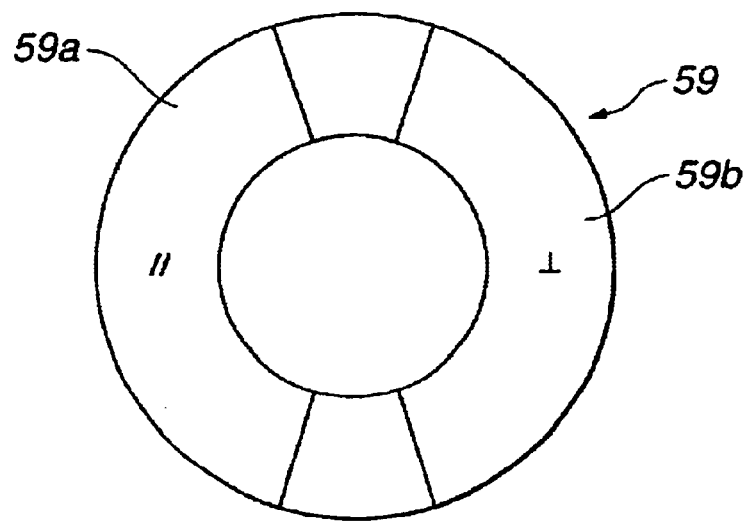

The construction of the rotating filter 59 is shown in FIG. 8. Polarizers 59a and 59b in the polarized light directions, which are orthogonal to each other, are mounted in the circumferential direction of the rotating filter 59. Here, for example, the polarizer 59a is set in the polarized light direction parallel to the polarized light direction of the polarizer 52. The other polarizer 59b is set in the polarized light direction orthogonal to the polarized light direction of the polarizer 52.

The light source device 3C has a construction without the light source aperture 43 in the light source device 3B of FIG. 5.

In the processor 4B of FIG. 5, the processor 4C is constituted such that the dual systems including the CCD drive circuits 31a and 31b, the A/D converting circuits 34a, 34b, and the color separating circuits 44a and 44b are changed to a single system (which is indicated by CCD drive circuit 31, A/D converting circuit 34, and color separating circuit 44). Output signals of the color separating circuit 44 are stored in the frame memories 36 and 36' through a multiplexer 35.

The control circuit 18 moves the movable stage 58 toward the bottom in the initial state, for example. Thus, the general-light observation mode is set where an image through the ocular lens 56 is formed in the full-color CCD 50 without passing through the rotating filter 59.

Also, in this case, the control circuit 18 controls the multiplexer 35 to store R, G and B color signal data from the color separating circuit 44 in the R, G and B planes of one frame memory 36. Also, in this case, the control circuit 18 R, G and B color signals read out from three planes (indicated by R, G and B planes) of the frame memory 36 are passed through and are output to the D/A converting circuit 38 side.

Then, analog R, G and B color signals converted by the D/A converting circuit 38 are output to the monitor 5. Thus, a general-light observation image, which is captured in full-color under general white light, is displayed in the monitor 5.

On the other hand, when the polarized-light image mode is selected through the mode switch 17, the control circuit 18 sets a state where the rotating filter 59 is disposed on an image-forming optical path of the image-forming lens 57, as shown in FIG. 6.

Furthermore, the control circuit 18 controls switching of the multiplexer 35. When signals representing images captured by the CCD 50 under the state where the polarizer 59a is disposed in the image-forming optical path, for example, are read out, the signals are written in the R, G and B planes of the frame memory 36.

On the other hand, when signals representing images captured by the CCD 50 under the state where the polarizer 59b is disposed in the image-forming optical path are read out, the control circuit 18 controls the switching of the multiplexer 35 so as to write them in the R, G and B planes of the frame memory 36'.

Furthermore, the control circuit 18 controls the image processing circuit 37, to which signals read out from the R, G and B planes of the frame memory 36 and the R, G and B planes of the frame memory 36' are input, so as to output after subtracting signals read out from the R, G and B planes of the frame memory 36' from the signals read out from the R, G and B planes of the frame memory 36.

In comparison with the embodiment in FIG. 5, this embodiment performs image capturing by using one full-color CCD 50. However, the same image is displayed in the monitor 5.

More specifically, in the general-light observation mode, first of all, the white light from the lamp 9 is transmitted by the light guide 49. Then, the light polarized by the polarizer 52 further illuminates the subject 53 from the distal end surface.

The light reflected by the subject 53 is formed into an image on the full-color CCD 50 through the objective lens 54, a relay lens 55 and so on. The signals photo-electrically converted in the full-color CCD 50 undergo A/D conversion, color separation and so on. Then, the signals are written in the frame memory 36. The signals read out from the frame memory 36 are converted to analog R, G and B color signals by the D/A converting circuit 38 and are displayed in the monitor 5.

In this case, the signals representing images captured by the full-color CCD 50 are equivalent to that produced by adding signals representing images captured by the CCD 27a and 27b in the embodiment in FIG. 5. Therefore, while the image processing circuit 37 is passed through in this embodiment, color signals output to the D/A converting circuit 38 side are equivalent to color signals, which undergo addition processing by the image processing circuit 37 in the general-light observation mode in FIG. 5 and are output to the D/A converting circuit 38 side.

Furthermore, in the polarized-light observation mode, signals representing images captured when the polarizer 59a of the rotating filter 59 is in the image-forming optical path, are stored in the R, G and B planes of the frame memory 36. Signals representing images captured when the polarizer 59b is in the image-forming optical path, are stored in the R, G and B planes of the frame memory 36'.

In this case, signals stored in the R, G and B planes of the frame memory 36 are equivalent to those representing images captured by the CCD 27a in the polarized-light observation mode in FIG. 5. Signals stored in the R, G and B planes in the frame memory 36' are equivalent to those representing images captured by the CCD 27b in the polarized-light observation mode in FIG. 5. Then, in this case, in the same manner as that of the case in FIG. 5, the same processing is performed in the image processing circuit 37 and thereafter.

According to this embodiment, a polarized-light image and a general-light observation image can be obtained by using the existing endoscope 46. Furthermore, according to this embodiment, the same image as that by the second embodiment can be obtained by using a single image pickup element and a signal processing system for the single image pickup element.

(Fourth Embodiment)

A fourth embodiment of the present invention will be described next with reference to FIG. 9. It is an object of this embodiment to provide an endoscope apparatus, which can obtain a polarized-light image and a general-light image by using an existing endoscope. This embodiment corresponds to a varied construction example of the endoscope in FIG. 6.

Figure 9:
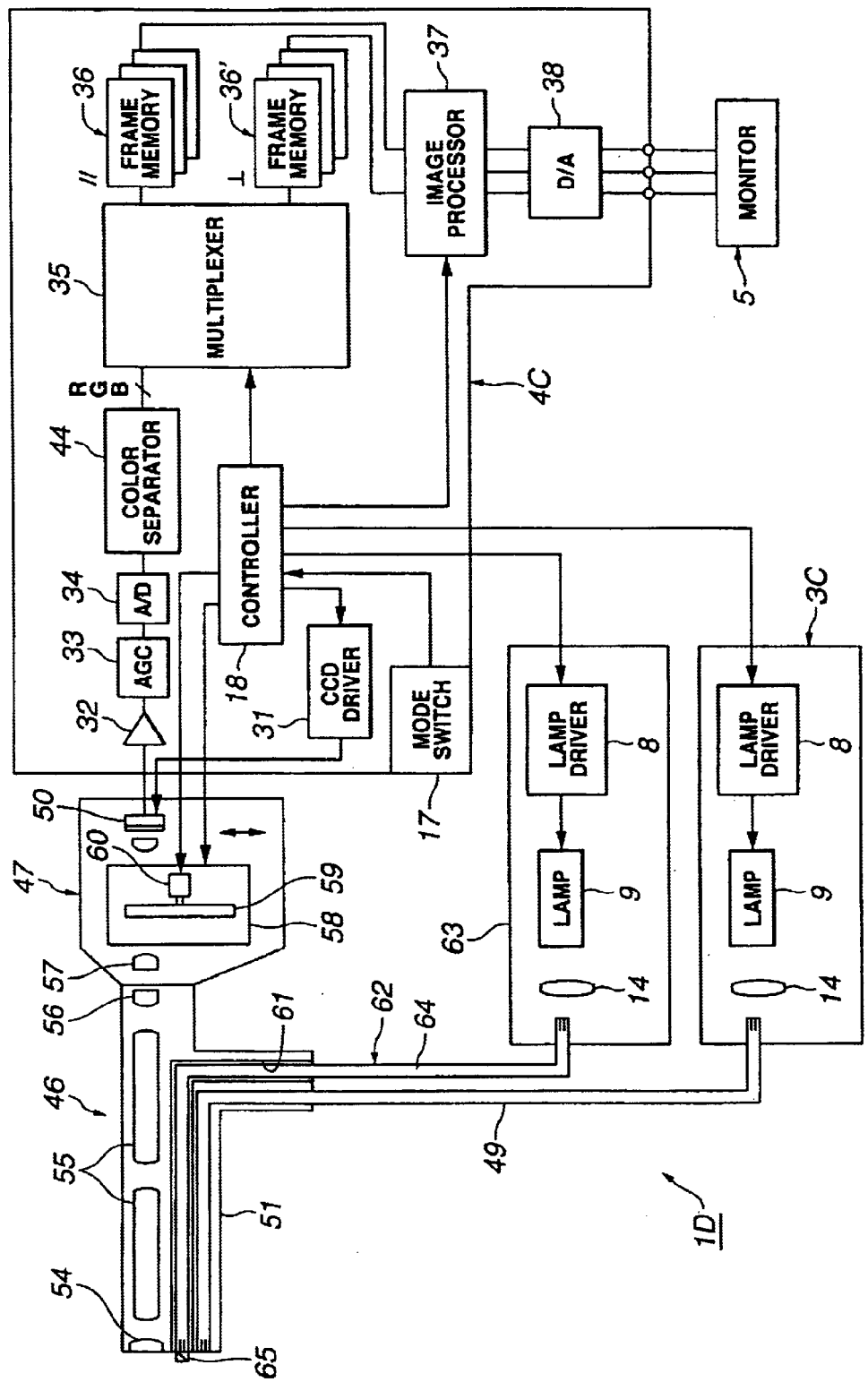
FIG. 9 is a block diagram showing an entire construction of an endoscope apparatus according to a fourth embodiment of the present invention.

In the endoscope apparatus 1C of FIG. 6, an endoscope apparatus 1D of the fourth embodiment shown in FIG. 9 inserts an optical probe 62 through a forceps channel 61, which is provided in the endoscope 46, without mounting and using the distal-end cap 48 in the endoscope 46. The optical probe 62 is connected to a light source device 63 for polarization, which is newly prepared.

The construction of the light source device 63 for polarization is the same as that of the light source device 3C in FIG. 6. Furthermore, the optical probe 62 includes a light guide 64 and a polarizer 65, which is mounted at the distal end of the light guide 64. Illuminating light from the light source device 63 for polarization is transmitted. Then, the polarized light from the distal end surface of the light guide 64 through the polarizer 65 is emitted.

In this case, the optical probe 62 is rotatable within the forceps channel 61. A polarizing direction of illuminating light to be rotated and polarized through the polarizer 65 can be adjusted to the direction parallel to the polarizing direction of the polarizer 59a of the rotating filter 59.

Notably, by providing, near the outlet of the forceps channel 61, an indicator, for example, for positioning the polarizing direction of the polarizer 65 to be parallel to the polarizing direction of the polarizer 59a of the rotating filter 59, the adjustment work can be omitted.

Furthermore, in this embodiment, lamp drive circuits 8 for the light source devices 3C and 63, respectively, are controlled by the control circuit 18. In other words, in the general-light observation mode, the lamp drive circuit 8 for the light source device 63 for polarization is set not to operate. Furthermore, in the general-light observation mode, the movable stage 58 and so on are controlled by the control circuit 18 in the same manner as that described in FIG. 6.

Furthermore, in the polarized-light observation mode, the lamp drive circuit 8 of the light source device 3C is set not to operate. In the polarized-light observation mode, the movable stage 58 and so on are controlled by the control circuit 18 in the same manner as that described in FIG. 6. The other construction is the same as that of the third embodiment.

The operations and the effects of this embodiment are basically similar to those of the third embodiment.

(Fifth Embodiment)

A fifth embodiment of the present invention will be described next with reference to FIGS. 10 to 12B. It is an object of this embodiment to provide an endoscope apparatus, which can obtain a polarized-light image and a general-light image by using an endoscope of one image pickup element (that is, an endoscope having an inserting portion, whose diameter can be narrowed).

Figure 10:
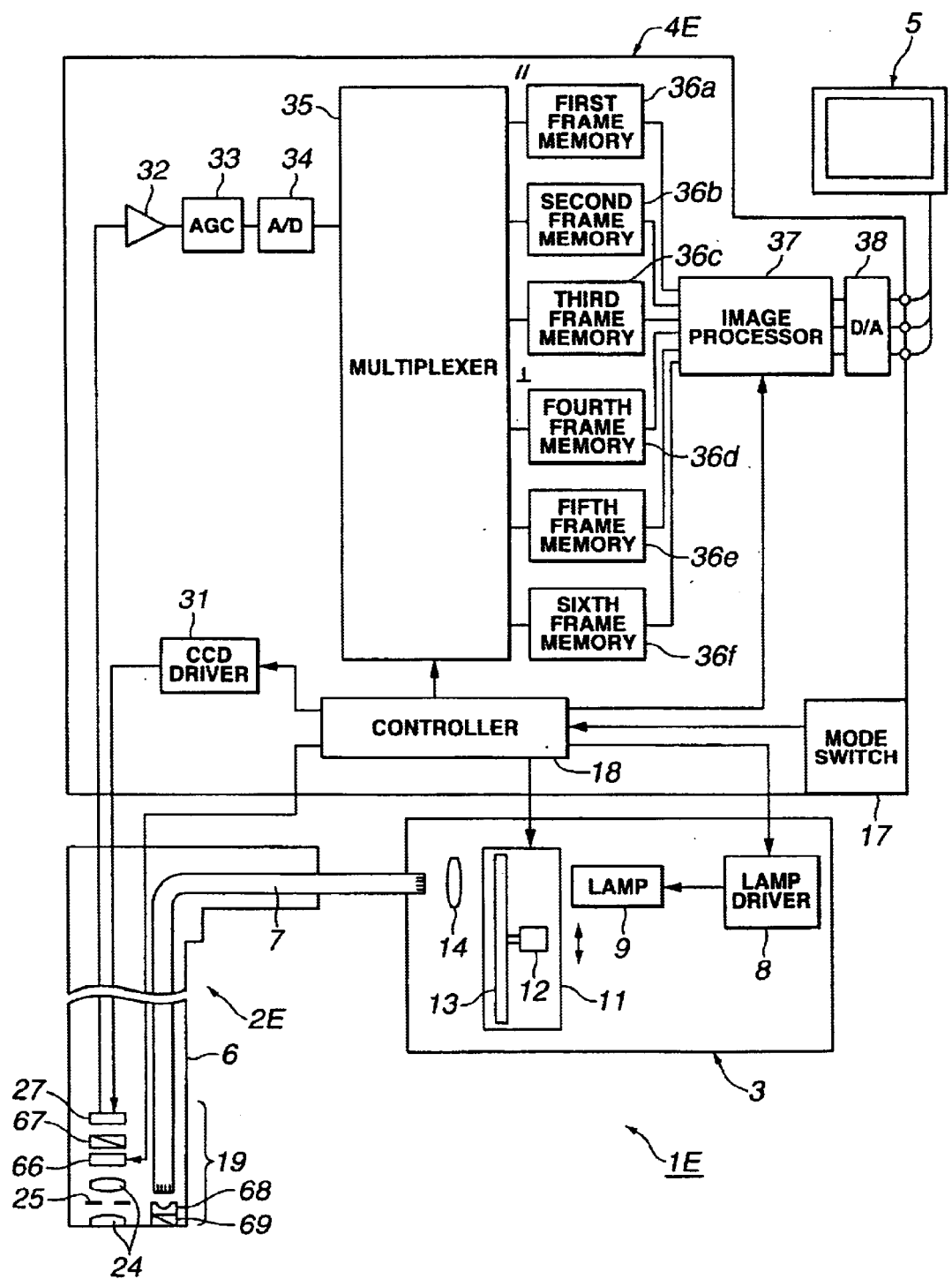

An endoscope apparatus 1E according to the fifth embodiment of the present invention shown in FIG. 10 includes an endoscope 2E, a light source device 3, a video processor 4E, and a monitor 5.

In the endoscope 2E, one CCD 27b in the endoscope 2 of FIG. 2 is removed and a single CCD 27 (there is only one CCD, so it is indicated by 27 instead of 27a) is left. Furthermore, liquid crystal (element) 66 and a polarizer 67 are disposed between the objective lens 24 and the CCD 27. The distal end of the light guide 7 is not bent and is arranged straight. An external subject or the like is illuminated from the distal end surface through an illuminating lens 68 and a polarizer 69 in this construction.

For the single CCD 27, the video processor 4E has a CCD drive circuit 31, a preamplifier 32, an AGC circuit 33 and an A/D converting circuit 34, all of which are single systems. Image data is written in first to sixth frame memories 36a to 36f through the multiplexer 35, which is switched by the control circuit 18.

The polarizing direction by a polarizer 67 disposed in front of the CCD 27 is set in parallel with the polarizing direction by the polarizer 69 disposed in front of the distal end surface of the light guide 7.

The liquid crystal 66 can be switched so as to rotate the polarizing direction by 0° and 90° in accordance with the presence of the application of a drive signal by the control circuit 18. In the general-light observation mode, the control circuit 18 does not drive the liquid crystal 66, for example. Thus, the incident light passes through the liquid crystal 66.

In this mode, the control circuit 18 switches the multiplexer 35 so as to store signals representing images captured under R, G and B illuminating light beams in the first frame memory 36a to the third frame memory 36c. Signals read out from the first frame memory 36a to the third frame memory 36c, respectively, pass through the image processing circuit 37 and are output to the D/A converting circuit 38 side.

On the other hand, in the polarized-light observation mode, the control circuit 18 performs alternately non-application and application of a drive signal to the liquid crystal 66 for every rotation of the rotating filter 13. When a state where a drive signal is not applied to the liquid crystal 66 and the polarizing direction is not changed is 0° (state) and a state where a drive signal is applied thereto and the polarizing direction is changed by 90° is 90° (state), the control circuit 18 stores in the first through sixth frame memories 36a to 36f signals representing images captured by the wavelengths in accordance with light transmittance wavelengths λ1, λ2, λ3, λ1 . . . due to the rotating filter 13, respectively, as shown in FIG. 11.

A polarized-light image obtained by subtraction by the image processing circuit 37, as described in the first embodiment, from signals read out from the first to sixth frame memories 36a to 36f, is displayed in the monitor 5.

According to this embodiment, the object can be achieved.

In other words, by using the endoscope 2E having one CCD 27 and the inserting portion 6 whose diameter can be narrowed, a general-light image and a polarized-light image can be captured. A general-light image and a polarized-light image can be displayed in the monitor 5 by performing signal processing thereon by the processor 4E.

Figure 12A:
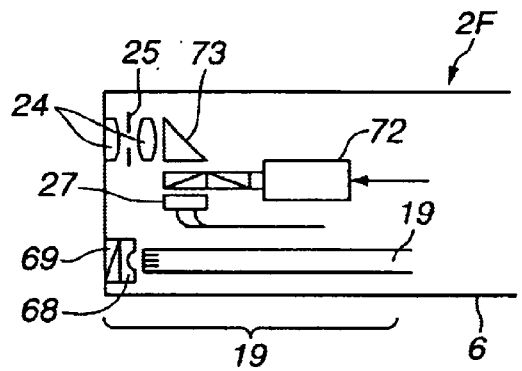
FIG. 12A is a diagram showing a construction of an endoscope distal end side in a variation example.

FIG. 12A shows a construction of the distal end side of an endoscope 2F in a variation example of the fifth embodiment. In this variation example, in the endoscope 2E of FIG. 10, two polarizers 71a and 71b having different polarizing directions instead of the liquid crystal 66 are disposed such that they can be moved by a piezoelectric actuator 72 and be switched into an image capturing optical path.

In this case, in order to make the direction of moving the polarizers by the piezoelectric actuator 72 to the axial direction of the inserting portion 6, light through the objective lens 24 is reflected by a triangular prism 73 and is conducted to the CCD 27 so as to construct as shown in FIG. 12A. As a result, one of the two polarizers 71a and 71b can be switched and disposed between the triangular prism 73 and the CCD 27 by the piezoelectric actuator 72.

Figure 12B:
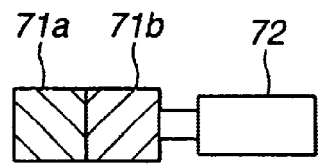

FIG. 12B shows the piezoelectric actuator 72 and the polarizers 71a and 71b, which are driven (moved) thereby, viewing from the above of FIG. 12A. The piezoelectric actuator 72 is driven by the control circuit 18 in the same cycle as that for driving the liquid crystal 66. The polarizers 71a and 71b are inserted and extracted into and from the image capturing optical path alternately.

Notably, regarding the polarizing directions of the polarizers 71a and 71b, the polarizer 71a is set to have the polarizing direction which is the direction of passing through light polarized by the polarizer 69 and the polarizer 71b is set to have the polarizing direction which is orthogonal to the polarizer 71a and is the direction of shutting light polarized by the polarizer 69.

Therefore, when the polarizer 71a is disposed between the triangular prism 73 and the CCD 27 as shown in FIG. 12A, for example, light polarized by the polarizer 69 is irradiated to the polarizer 71a. Then, a light component in which a polarizing direction is stored in light reflected from a subject is passed through. That is, it corresponds to the 0° state of the liquid crystal 66.

On the other hand, when the polarizer 71b is disposed between the triangular prism 73 and the CCD 27, it corresponds to the 90° state of the liquid crystal 66.

The operations and effects of this variation example are the same as those of the fifth embodiment.

(Sixth Embodiment)

A sixth embodiment of the present invention will be described next with reference to FIGS. 13 and 14. It is an object of this embodiment to provide an endoscope apparatus, which can obtain a polarized-light image and a general-light image by using an endoscope having one image pickup element (that is, an endoscope having an inserting portion, whose diameter can be narrowed).

Figure 13:
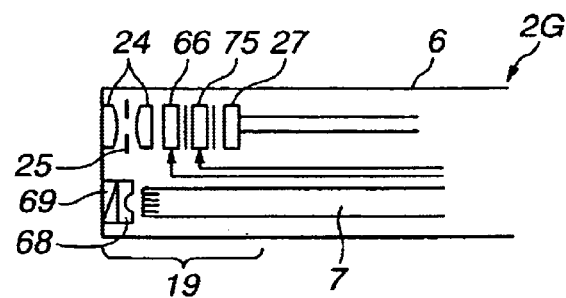
FIGS. 13 and 14 relate to a sixth embodiment of the present invention.

FIG. 13 shows a construction of a distal end side of an endoscope 2G according to the sixth embodiment. The endoscope 2G includes a liquid crystal tunable filter (called liquid crystal filter hereinafter simply) 75 for extracting (passing through) a component having a specific wavelength band, disposed between the liquid crystal 66 and the CCD 27 in the endoscope 2E of FIG. 10.

The liquid crystal 66 and the liquid crystal filter 75 are controlled by the control circuit 18, as described with reference to FIG. 14, which will be described later.

Notably, a light source device according to this embodiment is a general light source device in FIG. 10 in which the rotating filter 13 is only provided with R, G and B filters. However, in the polarized-light observation mode, the movable stage 11 is moved and the rotating filter 13 is evacuated from an optical path. Thus, white light from the lamp 9 is supplied by the focusing lens 14 to the light guide 7.

Figure 14:
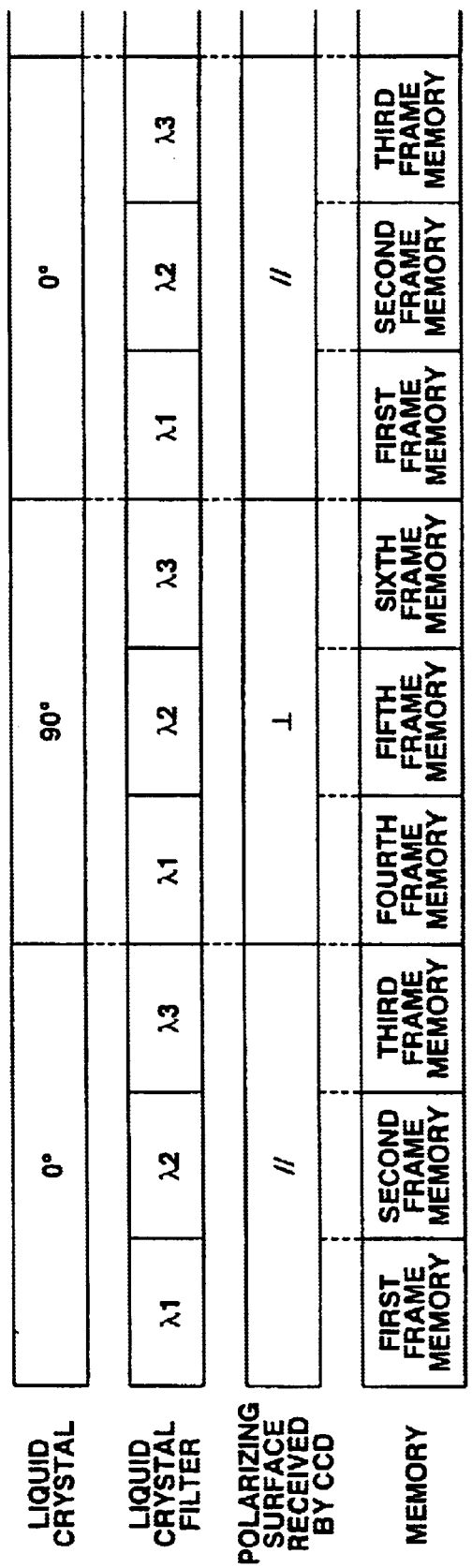

FIG. 14 shows an explanatory diagram of an operation in the polarized-light observation mode.

The liquid crystal 66 is set to 0° and 90° states alternately in the same cycle as that of the fifth embodiment. In each of the 0° and 90° states, the liquid crystal filter 75 is set to wavelengths λ1, λ2 and λ3 by the control circuit 18 sequentially.

In this case, when the liquid crystal 66 is in the 0° state, the light on the polarized-light surface received by the CCD 27 is reflected light (indicated by // in FIG. 14) retaining a polarized-wave surface, which is polarized by the polarizer 69.

When the liquid crystal 66 is in the 90° state, the light on the polarized-light surface received by the CCD 27 is reflected light (indicated by ⊥ in FIG. 14) orthogonal to a polarized-wave surface, which is polarized by the polarizer 69.

As shown in FIG. 14, signals output from the CCD 27 are written in the first to sixth frame memories 36a to 36f sequentially and then are written in the first to sixth frame memories 36a to 36f sequentially again.

The operations of the image processing device 37 and the operations thereafter are the same as those of the fifth embodiment.

This embodiment has substantially the same effects as those of the fifth embodiment.

(Seventh Embodiment)

Figure 15:
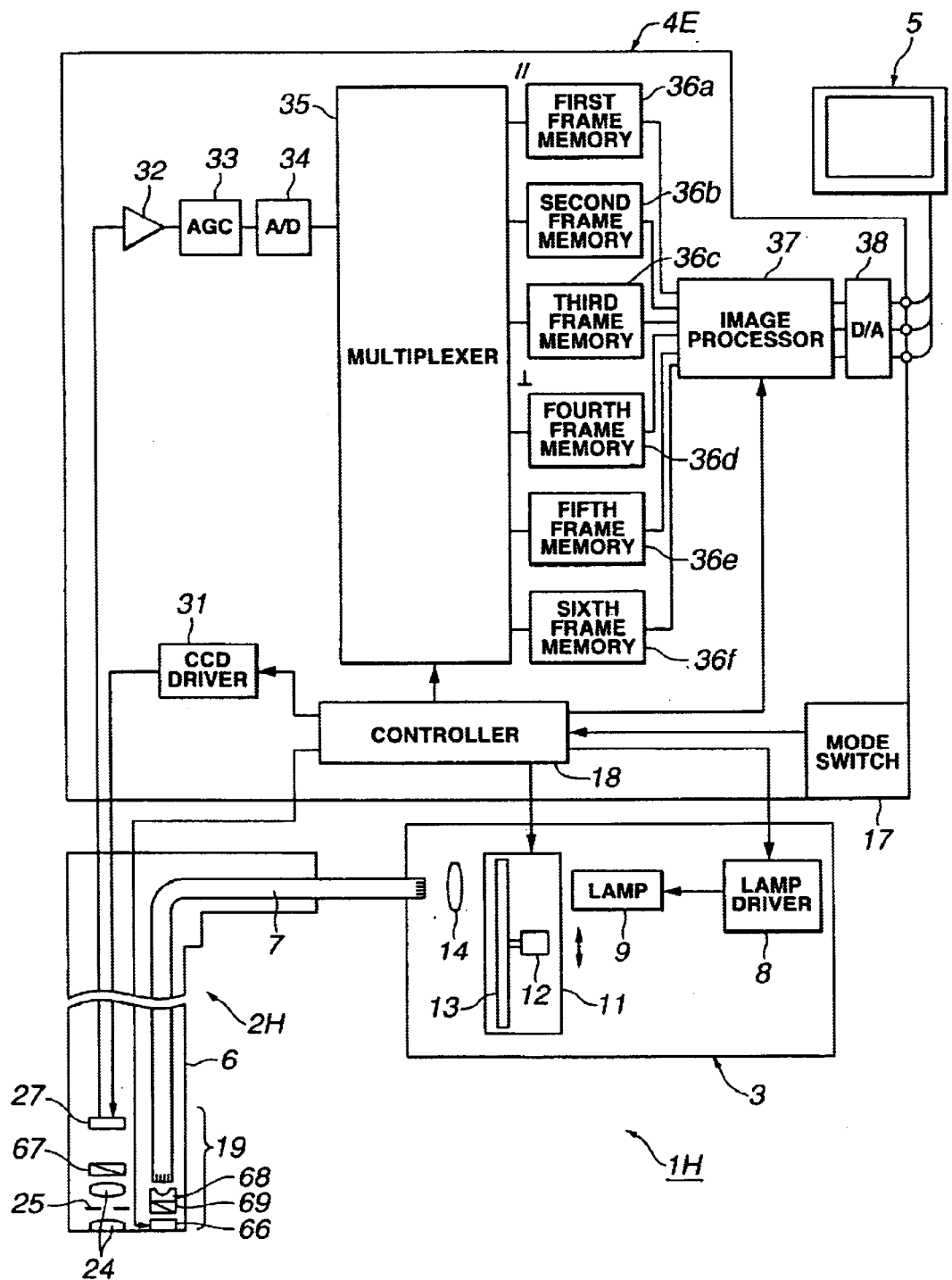
FIG. 15 is a block diagram showing an entire construction of an endoscope apparatus according to a seventh embodiment of the present invention.

A seventh embodiment of the present invention will be described next with reference to FIG. 15. In this embodiment, a direction of the polarized-light surface is changed in the illumination side for performing polarized-light observation. FIG. 15 shows an endoscope apparatus 1H according to the seventh embodiment of the present invention.

The endoscope apparatus 1H includes an endoscope 2H, a light source device 3, a video processor 4E and a monitor 5.

The endoscope 2H has liquid crystal 66 disposed in the illuminating side instead of the image capturing side in the endoscope 2E of FIG. 10. That is, the liquid crystal 66 is disposed in front of the polarizer 69, and a polarizing direction of the liquid crystal 66 is controlled by the control circuit 18. The other is the same as the construction in FIG. 10. The operations of this embodiment are also similar to those of the fifth embodiment.

In this case, in the polarized-light observation mode, light only having component with the polarizing direction of the illuminating light parallel to the polarizing direction of the polarizer 66, for example, is irradiated to a subject side and the image is captured by the CCD 27 through the polarizer 67. In this case, the CCD 27 captures an image by the polarized-light component parallel to the illuminating light. Then, image data captured by the CCD 27 is stored in the first to third frame memories 36a to 36c.

Then, a drive signal is applied to the liquid crystal 66 and light only having a component orthogonal to the polarizing direction of the polarizer 66 is irradiated to a subject side. Thus, image capturing is performed by the CCD 27 through the polarizer 67. In this case, the CCD 27 captures an image having a polarized-light component perpendicular to the illuminating light. Then, the image data obtained by the CCD 27 is stored in the fourth to sixth frame memories 36d to 36f.

These operations are repeated. The operations of the image processing device 37 and the operations thereafter are performed in the same manner as those of the fifth embodiment.

The effects of this embodiment are substantially the same as those of the fifth embodiment.

(Eighth Embodiment)

An eighth embodiment of the present invention will be described next with reference to FIGS. 16A to 17.

Figure 16A:
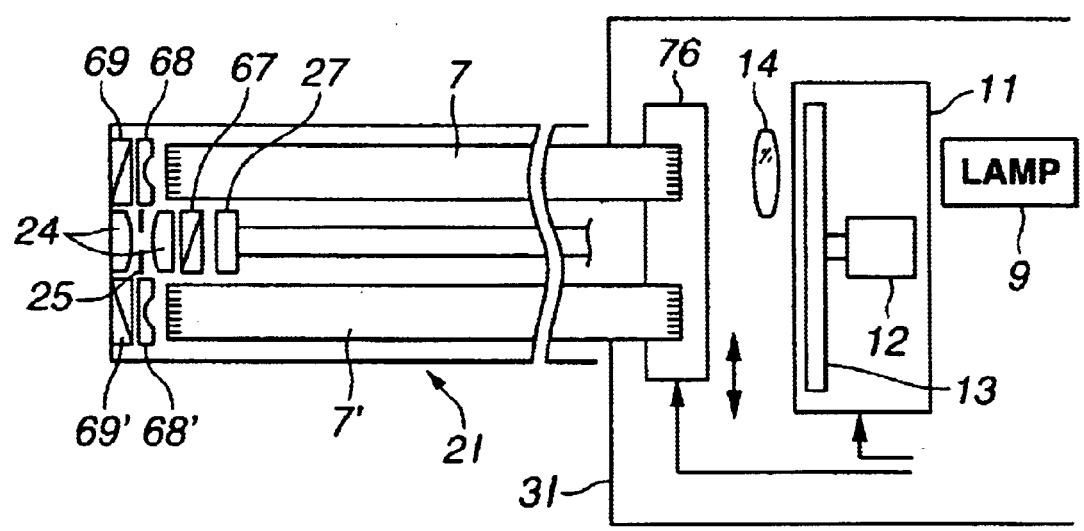

FIG. 16A shows a part of an endoscope 2I and a light source device 3I in an endoscope apparatus according to the eighth embodiment.

The endoscope 2I has a construction where the liquid crystal 66 is removed and a light guide 7' is provided in the endoscope 2E of FIG. 10, for example. An illuminating lens 68' and a polarizer 69' are provided in front of a distal end surface of the light guide 7'. The polarizing direction of the polarizer 69' is set to a direction orthogonal to the polarizing direction of the polarizer 69.

Figure 16B:
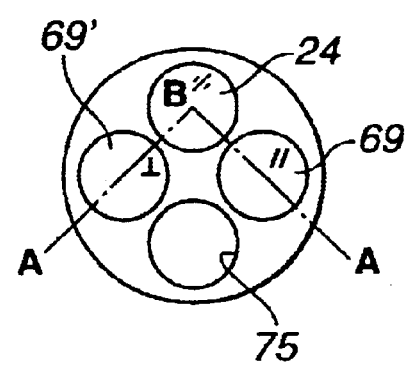
FIG. 16B is a front view of FIG. 16A.

FIG. 16B shows an arrangement of an optical system in a distal end surface, viewing from the front. An objective lens 24 is disposed in the upper part near the center between the polarizers 69 and 69', which are disposed symmetrically. A forceps channel 75 is disposed in the lower side of the objective lens 24. Notably, FIG. 16A shows a cross section taken by a line A-B-A in FIG. 16B.

The back ends of the light guides 7 and 7' are mounted at a movable stage 76, whose movement is controlled by the control circuit 18.

Then, in the polarized-light observation mode, the movable stage 76 is moved to a direction indicated by an arrow (up or down direction). Thus, illuminating light from the lamp 9 enters from one light guide to the other alternately in accordance with the state of the movement. The other is in the same construction as that of FIG. 10.

For example, in the state shown in FIG. 16A, light is entered to the light guide 7. In this state, the CCD 27 captures an image by the polarizing direction parallel to the polarizing direction of the illuminating light.

When the movable stage 76 is moved from the state, the illuminating light enters to the light guide 7'. Under this state, the CCD 27 captures an image by the polarizing direction perpendicular to the polarizing direction of the illuminating light.

This embodiment has substantially the same effects as those of FIG. 10.

Figure 17:
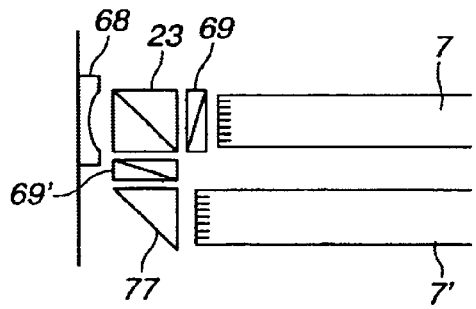

FIG. 17 shows a construction of an illuminating optical system in a distal end side of an endoscope in a variation example. In this case, the polarizer 69, a BS 23 and the illuminating lens 68 are disposed in front of the distal end surface of the light guide 7. A triangular prism 77 is disposed in front of the distal end surface of the light guide 7'. A polarizer 69' is disposed in a direction that light reflected by the triangular prism 77 goes so as to conduct the light to the BS 23. Then, the light passes through a common illuminating lens 68 for illumination. The BS 23 may be a polarizing beam splitter (PBS).

The other has the same construction as that of the case in FIG. 16. In addition, the same effects are achieved.

(Ninth Embodiment)

Figure 18:
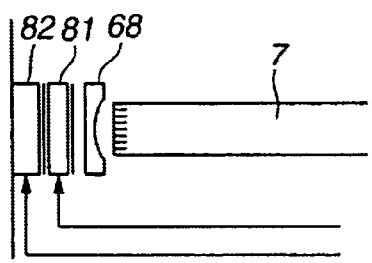
FIG. 18 is a diagram showing a construction of an illuminating optical system in an endoscope distal end side according to a ninth embodiment of the present invention.

FIG. 18 shows a construction of an illuminating optical system in a distal end side of an endoscope according to a ninth embodiment of the present invention. In this case, the rotating filter 13 including the movable stage 11 is removed from the light source device 3 in the endoscope apparatus 1H of FIG. 15, for example. The illuminating lens 68, a liquid crystal filter 81 and liquid crystal 82 are disposed in front of the the distal end surface of the light guide 7 in the endoscope 2H. A liquid crystal filter 81 and a liquid crystal 82 are controlled by the control circuit 18.

According to this embodiment, the same operations and effects as those of the case in FIG. 15 can be obtained in more simple construction.

(Tenth Embodiment)

Figure 19:
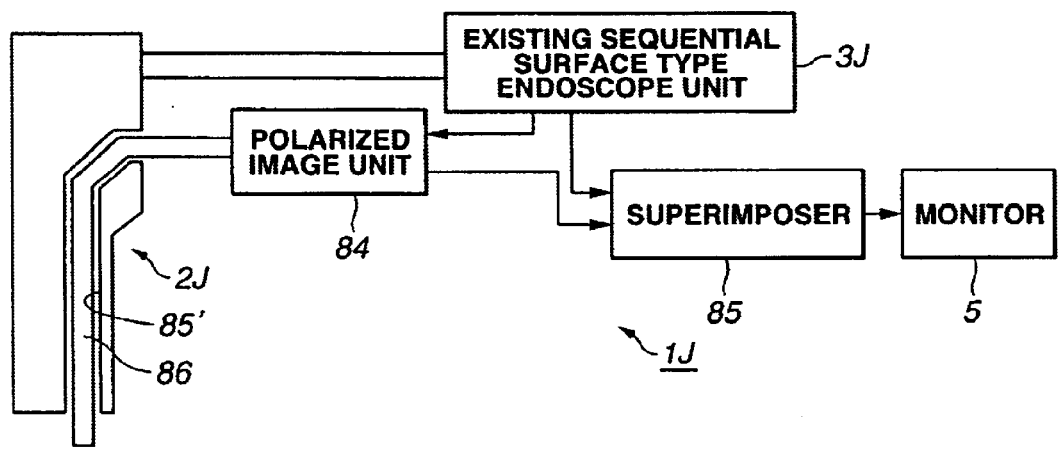
FIGS. 19 and 20 relate to a tenth embodiment of the present invention.

A tenth embodiment of the present invention will be described next with reference to FIGS. 19 and 20. It is an object of this embodiment to provide an endoscope apparatus, which allows polarized-light observation in low costs by being combined with an existing endoscope apparatus.

An endoscope system 1J of this embodiment includes an existing frame sequence type endoscope 2J, a frame sequence type endoscope unit 3J (which generates frame sequence type light and performs signal processing on signals captured in frames sequentially) used along with the existing frame sequence type endoscope 2J, a polarized image unit 84 for obtaining a polarized image, a superimposing circuit 85 for superimposing a polarized image obtained by the polarized image unit 84 and a general-light image obtained by the frame sequence type endoscope unit 3J, and a monitor 5 for displaying output signals of the superimposing circuit 85.

Figure 20:
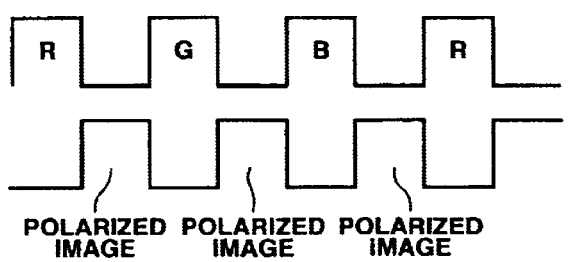

In this embodiment, as shown in FIG. 20, illumination is achieved by using R, G and B intermittently illuminated light beams. Signals are read out from the image pickup element during the light shutting period. However, during the light-shutting period, illumination and image capturing are performed for obtaining a polarized-light image by using a light guide 86, which is inserted through the forceps channel 85' of the endoscope 2J, by the image polarizing unit 84.

In order to obtain a polarized-light image during the light-shutting period, the frame sequence type endoscope unit 3J sends a synchronous signal to the image polarizing unit 84.

Then, a general-light image obtained in the case of frame sequence type illumination and a polarized-light image are superimposed in the superimposing circuit 85, which is displayed in the monitor 5.

The object is achieved by having such the construction as above.

(Eleventh Embodiment)

An eleventh embodiment of the present invention will be described next with reference to FIGS. 21 to 26. It is an object of this embodiment to provide a compound-eye endoscope apparatus (compound-eye stereoscopic microscope apparatus) for capturing a polarized-light image.

Figure 21:
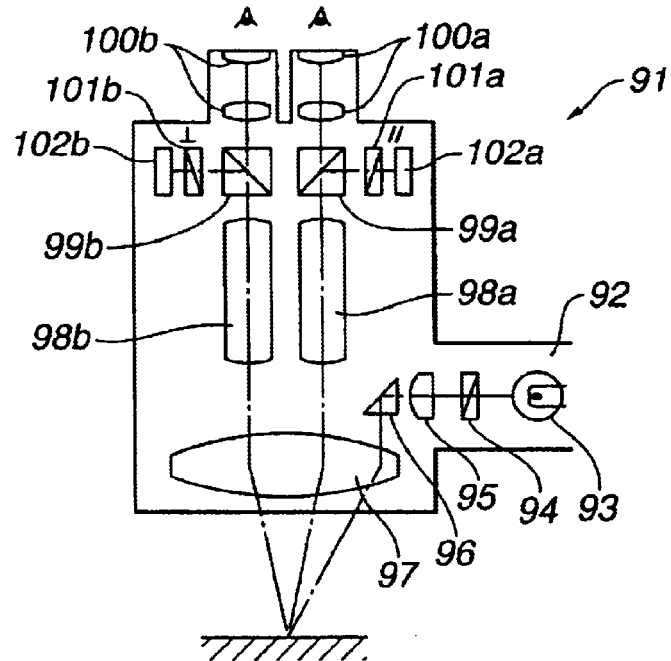

A compound-eye stereoscopic microscope 91 shown in FIG. 21 has a light source portion 92. Light from a lamp 93 included in the light source portion 92 is polarized in a polarizer 94 and is made to a parallel luminous flux in a collimate lens 95. The light path is changed by being reflected by a triangular prism 96. Then, the light is irradiated to a subject side through an opposite objective lens 97 having a large caliber.

The light, which is reflected in the subject side and is entered to an objective lens 97 enters to BS's 99a and 99b through relay lenses 98a ad 98b, which are disposed in parallel, respectively. A part of the light is transmitted and can be observed stereoscopically with the naked eyes through ocular systems 100a and 100b.

The light beams reflected by the BS's 99a and 99b form images in full-color CCD's 102a and 102b through polarizers 101a and 101b, respectively.

One polarizer 101a is set to be parallel to a polarizing direction of the polarizer 94. The other polarizer 101b is set in a direction orthogonal to the polarizing direction of the polarizer 94. Therefore, one full-color CCD 102a captures an image by reflected light parallel to the polarizing direction of the illuminating light.

The full-color CCD 102b captures an image by reflected light perpendicular to the polarizing direction of the illuminating light.

The full-color CCD's 102a and 102b are connected to the processor 4B in FIG. 5, for example. The output is displayed in the monitor 5. As such, the compound-eye stereoscopic microscope apparatus is formed.

According to this embodiment, the naked-eye observation can be performed by using a general compound-eye stereoscopic microscope, and a polarized-light image can be captured and be displayed.

Figure 22:
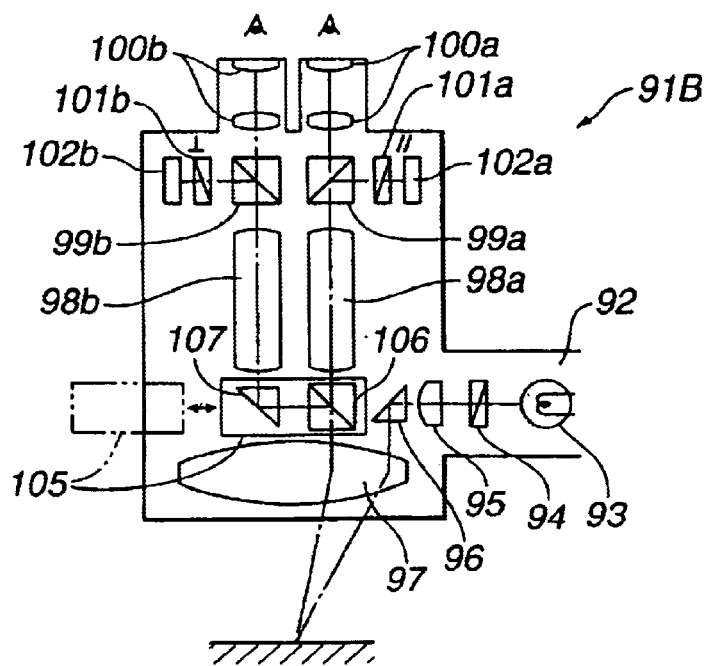

FIG. 22 shows a compound-eye stereoscopic microscope 91B in a variation example. In the case of the construction in FIG. 21, positions of polarized-light images obtained by the full-color CCD's 102a and 102b are different. In FIG. 22, a polarized-light image from the same position can be obtained.

In a compound-eye stereoscopic microscope 91B, an optical unit 105 for polarized-light observation can be freely inserted and extracted in an optical path between the objective lens 97 and the relay lenses 98a and 98b in the compound-eye stereoscopic microscope 91 of FIG. 21.

Under a condition where the optical unit 105 for polarized-light observation including the PBS 106 and the triangular prism 107 is attached (disposed) in an optical path, light in a polarizing direction parallel to a polarizing direction of illuminating light, incident on the PBS 106 through the objective lens 97 passes through the relay lens 98a side. On the other hand, the light, which is in a polarizing direction perpendicular to the polarizing direction of the illuminating light, is reflected and is further reflected by the triangular prism 107 and goes to the relay lens 98b side.

The same operations are performed in the relay lenses 98a and 98b and thereafter as those of FIG. 21.

The optical unit 105 for polarized-light observation, which is evacuated from the optical path, as indicated by a two-dotted line, can be used as a general compound-eye stereoscopic microscope.

A light-shield paint, for example, is painted on a part facing with the objective lens 97 below the triangular prism 107, for example, in the optical unit 105 for polarized-light observation. As indicated by a solid line in FIG. 22, light is shielded not to enter to the relay lens 98b directly through the objective lens 97 under a condition where the optical unit 105 for polarized-light observation is inserted in the optical path.

According to this embodiment, the naked-eye observation can be performed by using a general compound-eye stereoscopic microscope and a polarized-light image having no parallax displacement can be captured and displayed.

Figure 23:
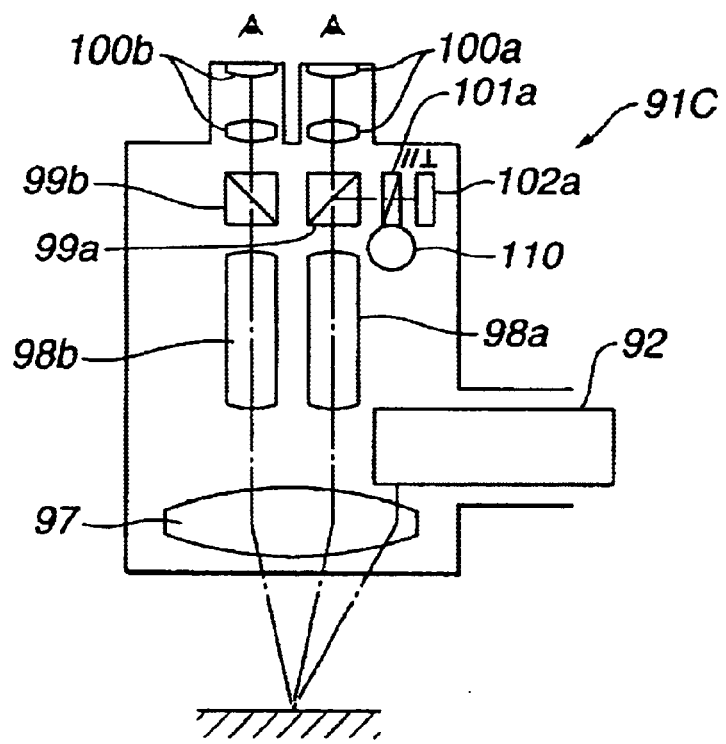

A compound-eye stereoscopic microscope 91C shown in FIG. 23 is adjusted to change a polarizing direction by rotating a polarizer 101a by a stepping motor 110 disposed between a BS 99a and a CCD 102a, for example, in the compound-eye stereoscopic microscope 91 in FIG. 21.

In this case, because of the construction for obtaining by CCD 102a an image in two polarizing directions, which are orthogonal, the other CCD 102b in FIG. 21 is not adopted.

The CCD 102a is connected to the processor 4C in FIG. 6, for example, and the output is output to the monitor 5.

Figure 24:
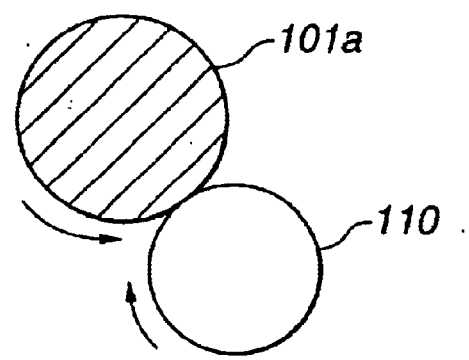

FIG. 24 shows a part, which allow changing a polarizing direction by rotating the polarizer 101a through rotation of the stepping motor 110.

As shown in FIG. 24, the polarizer 101a is rotated through the rotation of the stepping motor 110 and the polarizing direction is changed. The stepping motor 110 is rotationally driven by a motor drive circuit, not shown, under the control of the control circuit 18, for example.

In this case, the stepping motor 110 is temporarily terminated when the polarizer 101a is set at each of a rotational position (parallel position) parallel to a polarizing direction by the polarizer 94 of the light source portion 92 and a rotational position (vertical position) perpendicular to the polarizing direction thereof. Image data captured by the CCD 102a at the parallel position is stored in the frame memory 36.

On the other hand, the image data captured by the CCD 102a at the vertical position is stored in the frame memory 36'. Image data read out from both of the frame memories 36 and 36' undergo subtraction processing in the image processing circuit 37 in the same manner as one described in FIG. 6 and is D/A converted. Then, a polarized image is displayed in the monitor 5.

In this variation example, a polarized-light image is obtained by using one color CCD 102a.

FIG. 25A shows a state that a parallel polarized-light component and vertical component with respect to illuminating light can be made into an image by using one optical path in a microscope 111, which allows stereoscopic vision by using polarized light.

In order to obtain a stereoscopic image, the PBS 112 is used by being attached thereto, as shown in FIG. 25A.

Illuminating light from the light source portion 92, not shown, illuminates through the objective lens 97. The light beams in the left and right optical paths 117a and 117b are entered to the PBS 112 and the triangular prism 113 through the objective lens 97.

The light beam of the optical path 117a passes through the PBS 112. The light beam of the optical path 117b is reflected by the triangular prism 113. Each of the light beams is entered to the PBS 114 through the relay lens 98. Then, the light beam of the optical path 117a passes through the PBS 114 and goes to an ocular portion in the left eye side. The light beam of the optical path 117b is reflected by the PBS 114 and goes to an ocular portion in the right eye side through the triangular prism 115.

In order to obtain a polarized-light image, illuminating light polarized from the light source portion 92, not shown, illuminates through the objective lens 97. As shown in FIG. 25B, the PBS 112 is removed from the optical path (the removed state is shown by a two-dotted line). Full-color CCD's 116a and 116b are mounted in the ocular portions. The full-color CCD's 116a and 116b are connected to the processor 4B in FIG. 5. The output of the processor 4B is output to the monitor 5. Then, a polarized-light image is displayed in the monitor 5.

According to this variation example, stereoscopic observation becomes possible. In addition, a polarized-light image having no parallax displacement can be obtained.

FIG. 26 shows a compound-eye microscope apparatus 121, which can capture a polarized image. An optical path specifically for polarized-light images is provided between optical paths for stereoscopic vision in the apparatus 121.

In the apparatus 121, two relay lenses 98a and 98b for stereoscopic vision are disposed in parallel by facing with the objective lens 97. Shutters 122a and 122b and BS's 123a and 123b are disposed in the ocular side.

In addition, full-color CCD's 124a and 124b are disposed on an optical path in the reflecting side of the BS's 123a and 123b.

Furthermore, the center part of the objective lens 97 is cut and opened. A relay lens 125 for a polarized-light image is disposed along an optical axis of the objective lens 97. The shutters 122c and the PBS 126 are disposed in the ocular side. Light reflected by the PBS 126 is entered to the BS 123a. The light reflected by the BS 123a forms an image in the CCD 124a.

The light passing through the PBS 126 is reflected by a triangular prism 127 and is entered to the BS 123b. The light passing through the BS 123b forms an image in the CCD 124b.

The CCD's 124a and 124b are connected to the processor 4B in FIG. 5, for example and undergo signal processing. Then, an image is displayed in the monitor 5.

Then, for the stereoscopic vision, the shutters 122a and 122b are opened and the shutter 122c is closed such that the stereoscopic vision can be performed.

On the other hand, in order to obtain a polarized-light image, the shutters 122a and 122b are closed and the shutter 122c is opened such that a polarized-light image can be obtained from image data, which is captured by the CCD's 124a and 124b after passing through the specific relay lens 125.

Embodiments and the like constructed by combining each of the above-described embodiments and the like partially, for example, belong to the present invention.

Also having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus, comprising:
a light source device for generating general illuminating light for obtaining a general-light image and polarized image illuminating light having a plurality of wavelength bands for obtaining a polarized-light image;
an endoscope having:
a light conducting member for conducting the general illuminating light and the polarized image illuminating light,
a polarizing member for emitting polarized illuminating light, which is polarized through the light-conducting member, to a subject side; and
an image pickup device for outputting respectively a parallel image signal and a vertical image signal captured by using a light component in a polarizing direction parallel to a polarizing direction of the polarizing member and a light component in a polarizing direction perpendicular to the polarizing direction of the polarizing member, in light reflected by the subject side; and
an image processing device for performing image processing on at least one of the parallel image signal and the vertical image signal so that a general-light image can be displayed in a display device and for performing image processing on the parallel image signal and the vertical image signal so that a polarized-light image can be displayed in the display device.

2. The endoscope apparatus according to claim 1, wherein the light source device sequentially generates red, green and blue light beams as the general illuminating light and the polarized image illuminating light.

3. The endoscope apparatus according to claim 1, wherein the light source device generates white light as the general illuminating light.

4. The endoscope apparatus according to claim 1, wherein the light source device sequentially or simultaneously generates, as the polarized image illuminating light, light in a plurality of wavelength bands, whose reflection properties vary in accordance with whether living-body tissue is normal or is affected when a subject is the living-body tissue.

5. The endoscope apparatus according to claim 1, wherein the light in the plurality of wavelength bands is selected from between about 450 nm to 650 nm.

6. The endoscope apparatus according to claim 1, wherein the polarizing member includes a polarizer having a polarizing function, a polarizing beam splitter or a combination thereof.

7. The endoscope apparatus according to claim 1, wherein the image pickup device has two image pickup elements for creating the parallel image signal and the vertical image signal, respectively, or one image pickup element for commonly creating the parallel image signal and the vertical image signal.

8. The endoscope apparatus according to claim 1, wherein the image pickup device has a light-detecting member and an image pickup element for creating the parallel image signal and the vertical image signal, respectively.

9. The endoscope apparatus according to claim 8, wherein the light detecting member includes a polarizer, a polarizing beam splitter or a combination thereof.

10. The endoscope apparatus according to claim 8, wherein the light detecting member conducts a light component in a direction parallel to a polarizing direction of the polarized illuminating light to an image pickup element for parallel image capturing and for conducting a light component in a direction perpendicular to the polarizing direction of the polarized illuminating light to an image pickup element for vertical image capturing.

11. The endoscope apparatus according to claim 8, wherein the light-detecting member includes a first analyzer for conducting a light component in a direction parallel to the polarizing direction of the polarized illuminating light to a first image pickup element for parallel image capturing and a second analyzer for conducting a light component in a direction perpendicular to the polarizing direction of the polarized illuminating light to a second image pickup element for vertical image capturing.

12. The endoscope apparatus according to claim 8, wherein the light detecting member is a member, which can switch a polarizing direction, which periodically changes a time for conducting a light component in a direction parallel to the polarizing direction of the polarized illuminating light to an image pickup element and a time for conducting a light component in a direction perpendicular to the polarizing direction of the polarized illuminating light to the image pickup element.

13. The endoscope apparatus according to claim 1, wherein the image processing device creates differential image data produced by computing a difference between image data by the parallel image signal and image data by the vertical image signal.

14. The endoscope apparatus according to claim 13, wherein the image processing device creates the differential image data in the plurality of wavelength bands.

15. The endoscope apparatus according to claim 14, wherein the image processing device calculates a part satisfying a condition indicating wavelength dependency with respect to the differential image data in the plurality of wavelength bands, and the display device displays the part satisfying the condition.

16. The endoscope apparatus according to claim 1, wherein the image processing device has a frame memory for temporarily storing image data by the parallel image signal in the plurality of wavelength band and the image data by the vertical image signal.

17. The endoscope apparatus according to claim 1, further comprising a mode switching device for switching mode for causing a display device to display the general-light image and polarized-light images from the parallel image signal and the vertical image signal.

18. The endoscope apparatus according to claim 17, wherein the image processing device switches between processing for creating the general-light image and processing for creating a polarized-light image in response to a mode switching operation on the mode switching device.

19. The endoscope apparatus according to claim 1, wherein the endoscope includes a body of the endoscope, and a distal end member having the polarizing member removably at a distal end of the endoscope body.

20. The endoscope apparatus according to claim 1, wherein the endoscope includes an optical endoscope and a television camera, which is attached to an ocular portion of the optical endoscope and has an image pickup device built-in for capturing images by using a light component in a polarizing direction perpendicular to a polarizing direction of the polarizing member and for outputting a parallel image signal and a vertical image signal, respectively.

21. An endoscope freely removably connected to a light source device for generating general illuminating light for obtaining a general-light image and polarized image illuminating light having a plurality of wavelength bands for obtaining a polarized-light image, the endoscope comprising:

a light conducting member for conducting the general illuminating light and polarized image illuminating light, a polarizing member for emitting polarized illuminating light, which is polarized through the light-conducting member, to a subject side; and an image pickup device for outputting respectively a parallel image signal and a vertical image signal captured by using a light component in a polarizing direction parallel to a polarizing direction by the polarizing member and a light component in a polarizing direction perpendicular to the polarizing direction by the polarizing member, in light reflected by the subject side, wherein the endoscope is freely removably connected to an image processing device for performing on at least one of the parallel image signal and the vertical image signal so that a general-light image can be displayed in a display device, and for performing image processing on the parallel image signal and the vertical image signal so that a polarized-light image can be displayed in the display device.

22. The endoscope according to claim 21, wherein the polarizing member includes a polarizer having a polarizing function, a polarizing beam splitter or a combination thereof.

23. The endoscope according to claim 21, wherein the image pickup device has two image pickup elements for creating the parallel image signal and the vertical image signal, respectively, or one image pickup element for commonly creating the parallel image signal and the vertical image signal.

24. The endoscope according to claim 21, wherein the image pickup device has a light-detecting member and an image pickup element for creating the parallel image signal and the vertical image signal, respectively.

25. The endoscope according to claim 24, wherein the polarizing member includes a polarizer having a polarizing function, a polarizing beam splitter or a combination thereof.

26. The endoscope according to claim 24, wherein the light-detecting member conducts a light component in a direction parallel to a polarizing direction of the polarized illuminating light to an image pickup element for parallel image capturing and for conducting a light component in a direction perpendicular to the polarizing direction of the polarized illuminating light to an image pickup element for vertical image capturing.

27. The endoscope according to claim 24, wherein the light-detecting member includes a first analyzer for conducting a light component in a direction parallel to the polarizing direction of the polarized illuminating light to a first image pickup element for parallel image capturing and a second analyzer for conducting a light component in a direction perpendicular to the polarizing direction of the polarized illuminating light to a second image pickup element for vertical image capturing.

28. The endoscope according to claim 24, wherein the light detecting member is a member, which can switch a polarizing direction, which periodically changes a time for conducting a light component in a direction parallel to the polarizing direction of the polarized illuminating light to an image pickup element and a time for conducting a light component in a direction perpendicular to the polarizing direction of the polarized illuminating light to the image pickup element.

29. An image processing device freely removably connected to an endoscope including an image pickup device for outputting a parallel image signal and a vertical image signal captured by using a light component in a polarizing direction parallel to a polarizing direction by the polarizing member and a light component in a polarizing direction perpendicular to the polarizing direction by the polarizing member, respectively, in light reflected by a subject side, the image processing device performing on at least one of the parallel image signal and the vertical image signal so that a general-light image can be displayed in a display device, and for performing image processing on the parallel image signal and the vertical image signal so that a polarized-light image can be displayed in the display device.

30. The image processing device according to claim 29, which creates differential image data produced by computing a difference between image data by the parallel image capturing signal and image data by the vertical image signal.

* * * * *